US005942489A

United States Patent [19]
Schally et al.

[11] Patent Number: 5,942,489
[45] Date of Patent: Aug. 24, 1999

[54] HGH-RH(1-29)NH2 ANALOGUES HAVING ANTAGONISTIC ACTIVITY

[75] Inventors: Andrew V. Schally, Metairie, La.; Marta Zarandi, Szeged, Hungary; Katalin Toth, Metairie, La.

[73] Assignee: The Administrators of the Tulane Educational Fund, New Orleans, La.

[21] Appl. No.: 08/642,472

[22] Filed: May 3, 1996

[51] Int. Cl.⁶ .......................... A61K 38/16; A61K 38/12; C07K 7/64; C07K 7/00
[52] U.S. Cl. .................. 514/11; 514/9; 514/12; 530/317; 530/324
[58] Field of Search .................. 530/324, 317; 514/9–11, 12

[56] References Cited

U.S. PATENT DOCUMENTS

| | | | |
|---|---|---|---|
| 4,377,515 | 3/1983 | Veber et al. | 260/112.5 LH |
| 4,493,934 | 1/1985 | Veber et al. | 548/550 |
| 5,358,934 | 10/1994 | Borovsky et al. | 514/17 |
| 5,516,759 | 5/1996 | Swenson et al. | 514/15 |
| 5,550,212 | 8/1996 | Zarandi et al. | 530/324 |
| 5,723,614 | 3/1998 | Bathe et al. | 544/376 |

FOREIGN PATENT DOCUMENTS

| | | |
|---|---|---|
| 0352014 | 7/1989 | European Pat. Off. . |
| 0365779 | 8/1989 | European Pat. Off. . |
| 91/16923 | 11/1991 | WIPO . |
| 9516707 | 6/1995 | WIPO . |

OTHER PUBLICATIONS

Rekasi, Z. A method for evaluation of activity of antagonistic analogs of growth hormone–releasing hormone in a superfusion system. Proc. Natl. Acad. Sci. U. S. A. 90(6), 2146–2149, Jun. 1993.

Zarandi, M.; Horvath, J. E.; Halmos, G.; Pinski, J., Nagy, A.; Groot, K,; Rekasi, Z.; Schally, A. V. Synthesis and biological activities of highly potent antagonists of growth hormone–r-eleasing hormone. Proc. Natl. Acad. Sci. U. S. A. (1994), 91(25), Aug. 1, 1994.

Sato, K., Hotta, M., Kageyama J., Hu, H., Dong, M., Ling, N. Synthetic analogs of growth hormone–releasing factor with antagonistic activity in vitro. Biochem. Biophys. Res. Commun. 167(1), 360–6, Jan. 1990.

Sato, K., Hotta, M., Kageyama, J., Chiang, T., Chang; H., Hsiao Y., Dong, M., Ling, N. Structure–activity relations of growth hormone–releasing factor. Pept. Chem., vol. Date 1988, 26th, 85–90, 1989.

Schally A. et al. In: Growth hormone secretagogues in clinical practice. B. Bercu & R. Walker, Eds. Marcel Dekker, N.Y., chapter 10, pp. 145–162, Jan. 1998.

Fry D.C. et al. Biopolymers, 32(6) 649–666, Jun. 1992.

Felix A.M. et al. Abstr.Pap.Am.Chem.Soc. (199 Meet., Pt. 1, BIOL130,) Feb. 1990.

Notification of Transmittal of Search Report, Oct. 1, 1997.

Proc. Natl. Acad Sci, vol. 91, pp. 12298–12303, Dec. 1994.

Peptides, vol. 18, No. 3, pp. 423–440, 1997.

Peptides, vol. 18, No. 3, pp. 431–438, 1997.

*Primary Examiner*—Cecilia J. Tsang
*Assistant Examiner*—Michael Borin
*Attorney, Agent, or Firm*—Omri M. Behr, Esq.

[57] ABSTRACT

A peptide selected from the group having the formulae:
α) $X-R^1-R^2-R^3-R^4-R^5-R^6-Thr-R^8-R^9-R^{10}-R^{11}-R^{12}-Val-Leu-R^{15}-Gln-Leu-Ser-R^{19}-R^{20}-R^{21}-Leu-Leu-Gln-Asp-Ile-R^{27}-R^{28}-R^{29}$, wherein X is H, Ac, Aqc, IAc, BrProp, For, Ibu, Nac, 2-Nac, 1- or 2-Npt, 1- or 2-Npr, PhAc, Fpr, or any other aromatic or nonpolar acyl group, $R^1$ is Tyr, His or Phe(Y), in which Y=H, F, Cl, Br, $NO_2$, $CH_3$ or $OCH_3$, $R^2$ is D-Arg, D-Cit, D-Har, D-Lys, D-Tic or D-Orn, $R^3$ is Asp, D-Asp, Ala, D-Ala or Gly, $R^4$ is Ala, Abu or Gly, $R^5$ is Ile, Ala or Gly, $R^6$ is Phe, Tic, Ala, Pro, Tpi, Nal or Phe(Y), in which Y=H, F, Cl, Br, $NO_2$, $NH_2$, $CH_3$ or $OCH_3$, $R^8$ is Asn, Gln, Ser, Thr, Val, Leu, Ile, Ala, D-Ala, D-Asn, D-Gln, D-Thr, D-Leu, Abu, D-Abu, Nle, or Alb, $R^9$ is Ser, $R^{10}$ is Tyr or Phe(Y), in which Y=H, F, Cl, Br, $NO_2$, $CH_3$ or $OCH_3$, $R^{11}$ is Arg, D-Arg, or Cit, $R^{12}$ is Lys, D-Lys, Cit, D-Cit, Orn, D-Orn, Nle or Ala, $R^{15}$ is Gly, Ala, Abu or Gln, $R^{19}$ is Ala or Abu, $R^{20}$ is Arg, D-Arg or Cit, $R^{21}$ is Lys, D-Lys, Orn or Cit, $R^{27}$ is Met, Nle or Abu, $R^{28}$ is Ser, Asn, Ala or Abu, $R^{29}$ is Agm, $Arg-NH_2$, Arg-OH, $Cit-NH_2$, Cit-OH, $Har-NH_2$ or Har-OH, and β) $X-A^1-B^2-A^3-R^4-R^5-R^6-Thr-A^8Ser-R^{10}-R^{11}-B^{12}-Val-Leu-R^{15}-A^{16}-A^{17}-Ser-R^{19}-B^{20}-B^{21}-Leu-Leu-Gln-A^{26}-Ile-R^{27}-R^{28}-R^{29}$, wherein a lactam bridge is formed between any one of the pairs of positions 1,2; 2,3; 8,12; 16,20; 17–21; 21,25; 25,29 or both 8,12 and 21,25 positions, and X is H, Ac, Aqc, IAc, BrProp, For, Ibu, Nac, 2-Nac, 1- or 2-Npt, 1- or 2-Npr, PhAc, Fpr, or any other aromatic or nonpolar acyl group, A is Glu, D-Glu, Gln, Asp, D-Asp, Asn, Abu, Leu, Tyr, His, Phe(Y), in which Y=H, F, cl, Br, $NO_2$, $NH_2$, $CH_3$ or $OCH_3$, Ser, Thr, Val, Ile, Ala, D-Ala, D-Asn, D-Gln, D-Thr, D-Leu, Abu, D-Abu, Nle, or Aib, B is Lys, D-Lys, Arg, D-Arg,Orn, D-Orn, or Agm; $R^4$ is Ala, Abu or Gly, $R^5$ is Ile, Ala or Gly, $R^6$ is Phe, Tic, Tpi, Nal or Phe(Y), in which Y=H, F, Cl, Br, $NO_2$, $NH_2CH_3$ or $OCH_3$, $R^{10}$ is Tyr or Phe(Y), in which Y=H, F, Cl, Br, $NO_2$, $NH_2CH_3$ or $OCH_3$, $R^{15}$ is Gly, Ala, Abu or Gin, $R^{27}$ is Met, Nle or Abu, $R^{28}$ is Ser, Asn, Asp, Ala or Abu, and pharmaceutically acceptable salts thereof.

20 Claims, 1 Drawing Sheet

HGH-RH(1-29)NH2 ANALOGUES HAVING ANTAGONISTIC ACTIVITY

FIELD OF INVENTION

This invention was made in part with Government support from the Medical Research Service of the Veterans Affairs Department. The Government has certain rights in this application.

The present invention relates to novel synthetic peptides which inhibit the release of growth hormone from the pituitary in mammals, and to therapeutic compositions containing these novel peptides.

BACKGROUND OF THE INVENTION

Growth Hormone ("GH") is a peptide having 191 amino acids which stimulates the production of numerous different growth factors, e.g. IGF-I and so promotes growth of numerous tissues (skeleton, connective tissue, muscle and viscera) and physiological activities (raising nucleic acid and protein synthesis and lipolysis, but lowering urea secretion).

Release of GH is under the control of releasing and inhibiting factors secreted by the hypothalamus. The primary releasing factor is growth hormone releasing hormone ("GH-RH"); human growth hormone-releasing hormone ("hGH-RH") is a peptide having 44 amino acids. The novel peptides of the present invention relate to analogues of hGH-RH having only residues 1 through 29 ("hGH-RH (1–29)NH$_2$"), i.e., to analogues of the peptide which has the amino acid sequence:

Tyr-Ala-Asp-Ala-Ile$^5$-Phe-Thr-Asn-Ser-Tyr$^{10}$-Arg-Lys-Val-Leu-Gly$^{15}$-Gln-Leu-Ser-Ala-Arg$^{20}$-Lys-Leu-Leu-Gln-Asp$^{25}$-Ile-Met-Ser-Arg$^{29}$-NH$_2$

GH has been implicated in several diseases. One disease in which GH is involved is acromegaly, in which excessive levels of GH are present. The abnormally enlarged facial and extremity bones of this disease can be treated by administering a GH-RH antagonist.

Further diseases involving GH are diabetic retinopathy and diabetic nephropathy. The damage to the retina and kidneys respectively in these diseases, believed to be due to GH, results in blindness or reduction in kidney function. This damage however can be prevented or slowed by administration of an effective GH-RH antagonist.

In an effort to intervene in these disease and other conditions, some investigators have attempted to control GH levels by using somatostatin, one inhibitor of GH release. However, somatostatin, if administered alone, does not suppress GH or IGF-I levels to a desired degree. If administered in combination with a GH-RH antagonist, somatostatin would improve suppression of IGF-I levels much better.

Other workers have investigated various modifications of GH-RH to elucidate the relationship of the structure of GH-RH to its activity in an effort to provide synthetic congeners with improved agonistic or antagonistic properties. (Synthesis may be by solid phase method, described in U.S. Pat. No. 4,914,189, or in liquid phase, as described in U.S. Pat. No. 4,707,541.) Thus, in one study, it was found that synthesizing GH-RH without its N-terminus residue— i.e., forming hGH-RH(2–44)—results in an analogue having GH releasing activity which is only 0.1% that of GH-RH. By contrast, synthesizing a GH-RH analogue without its residues 30 through 44—i.e., synthesizing hGH-RH(1–29) NH$_2$—results in an analogue which retains 50% or more of the potency of native hGH-RH. Synthesizing even shorter analogues—e.g., GH-RH(1–28)NH$_2$ or GH-RH(1–27) NH$_2$—resulted in substantially lower bioactivity. These results indicate that sequence 1–29 is important to the bioactivity of GH-RH.

In another study, it was found that acetylating the N-terminus amino acid residue of GH-RH or replacing it with a D-isomer—thus forming [Ac-Tyr$^1$]GH-RH or [D-Tyr$^1$]GH-RH—lowers the ability of the analogues to release GH to 2–3% that of GH-RH. These analogues also have less affinity in vitro for GH-RH binding sites. By contrast, acetylation of the alpha amino group of residue 1 in hGH-RH(1–29)NH$_2$—thus forming [AcTyr$^1$]hGH-RH (1–29)NH$_2$—is found to raise the in vivo potency over that of GH-RH by ten fold or more.

In further studies, it was found that [Ac-Tyr$^1$,D-Arg$^2$] hGH-RH(1–29) NH$_2$ antagonizes the activation of rat anterior pituitary adenylate cyclase by hGH-RH(1–29)NH$_2$. The same peptide was found to block the action of GH-RH on its receptors in the pituitary and hypothalamus, and to inhibit the pulsatile growth hormone secretion.

Several reported modifications to GH-RH have resulted in agonistic activity. U.S. Pat. No. 4,659,693 discloses agonists of hGH-RH(1–29) having the formula:

R$^1$-R$^2$-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-R$^{27}$-Ser-Arg-NH$_2$, wherein R$^1$ is H, Tyr or His; R$^2$ may be various residues; and R$^{27}$ is Nle. These agonists are said to stimulate release of growth hormone releasing factor ("GRF") and so to be suitable in pharmaceutical compositions. ("GRF" is merely a synonym for GH-RH, and the latter abbreviation is used hereinafter, despite use of GRF in U.S. Pat. No. 4,659,693 and other publications.)

U.S. Pat. No. 4,914,189 discloses other analogues of GH-RH which are agonists. In these agonists, the N-terminus group Q$^1$CO—, where Q$^1$ signifies certain omega or alpha-omega substituted alkyl groups, may be Tyr or des-amino-Tyr; the C-terminus group NH-Q$^2$, where Q$^2$ signifies certain lower omega-guanidino-alkyl groups, may be Agm; and R$^{27}$ may be Nle. These analogues are said to be extremely potent stimulants of GH release and to enjoy high resistance to in vivo enzymatic degradation due to the omega-guanidino-lower alkyl group at the C-terminus.

Published application WO 91/16923 reviews earlier attempts to alter the secondary structure of hGH-RH by modifying its amino acid sequence. These earlier attempts include: replacing Tyr$^1$, Ala$^2$, ASp$^3$ or Asn$^8$ with their D-isomers; replacing Ser$^9$ with Ala to enhance amphilicity of the region; and replacing Asn$^8$ with L- or D-Ser, D-Arg, Asn, Thr, Gln or D-Lys. Certain of these modifications are said to enhance GH releasing activity. WO 91/16923 also states that replacing Asn$^8$ with Ala induces an enormous increase in GH releasing activity. The peptides said to have this benefit have the formula:

[R$^1$,R$^2$,Ala$^8$,R$^{15}$,Nle$^{27}$]hGH-RH(1–29)-NH$_2$, where R$^1$ is Dat or A-R$^1$, where A is lower acyl or benzyl and R$^1$ includes Tyr and His; R$^2$ is Ala, D-Ala or N-Me-D-Ala (N-Methyl-D-Ala); and R$^{15}$ may include Gly, Ala or Aib. One preferred embodiment has R$^{8,9,15}$ as Ala. It is noted that R$^8$ in this publication is never Asn. Pharmaceutical compositions for enhancing growth are further disclosed.

European Patent Application Ser. No. 0 413 839 A, filed Aug. 22, 1989, assigned to the same assignee as the present application, discloses analogues of hGH-RH(1–29)-NH$_2$ said to have enhanced release of GH. The 29 as follows: R$^1$ may be Tyr or Dat; R$^2$ may be L or D Ala; R$^8$ may be Asn or Ser; R$^{12}$ may be L or D isomers of Lys, Arg or Orn; R$^{15}$ may be Gly or Ala; R$^{27}$ may be Nle; R$^{28}$ may be Asp, Asn or Ser; and $R^{29}$ may be Agm. However, residue 6 is never replaced: it is always Phe.

Yet another modification of hGH-RH was disclosed in U.S. Pat. No. 5,183,660, where GH-RH was conjugated with polyethylene glycol derivatives. The resulting conjugate was said to exhibit decreased antigenicity, delay in biological clearance in vivo and physiological activity over a longer time.

In several of these investigations, it was found that variants of the hGH-RH agonistic analogues had antagonistic, rather than agonistic, activity. Thus, in U.S. Pat. No. 4,659,693 (where $R^2$ may be certain D-Arg residues substituted with alkyl groups), when $R^1$ is H, the hGH-RH analogues are said to act as antagonists. Similarly, in WO 91/16923, discussed above, if $R^2$ in the analogues is D-Arg, and $R^8$, $R^9$, and $R^{15}$ are substituted as indicated above, antagonistic activity is said to result. These antagonistic peptides are said to be suitable for administration as pharmaceutical compositions to treat conditions associated with excessive levels of GH, e.g., acromegaly.

The antagonistic activity of the hGH-RH analogue "[Ser$^9$-ψ[CH$_2$—NH]-Tyr]hGH-RH(1–29)" of U.S. Pat. No. 5,084,555 was said to result from the pseudopeptide bond (i.e., a peptide bond reduced to a [CH$_2$—NH] linkage) between the $R^9$ and $R^{10}$ residues. (It is noted that although this patent employed the seemingly redundant "ψ[CH$_2$—NH]" formula for the pseudo-peptide bond, actually only one such linkage had been introduced into the peptide.) However, the antagonistic properties of [Ser$^9$-ψ[CH2—NH]-Tyr$^{10}$]hGH-RH (1–29) were said to be inferior to a conventional antagonist, [N-Ac-Tyr$^1$, D-Arg$^2$]GH-RH(1–29)-NH$_2$.

U.S. Pat. No. 5,084,442 discloses cyclic lactam analogues of GH-RH which are agonists. The introduction of lactam bridge into peptides or proteins is known to reduce the number of possible conformations. Incorporation of constraints into biologically active peptides may improve receptor binding and result in analogs which have enhanced or prolonged biological activity.

SUMMARY OF THE INVENTION

There is provided a novel series of synthetic analogues of hGH-RH(1–29)NH$_2$. These analogues inhibit the activity of endogenous hGH-RH, and therefore prevent the release of growth hormone. This inhibition is believed to result from replacement of various amino acids and acylation with aromatic or nonpolar acids at the N-terminus of GH-RH (1–29)NH$_2$. The analogues exhibit prolonged antagonistic duration.

Specifically, the invention relates to peptides comprising the formulae:

α) X-R$^1$-R$^2$-R$^3$-R$^4$-R$^5$-R$^6$-Thr-R$^8$-R$^9$-R$^{10}$-R$^{11}$-R$^{12}$-Val-Leu-R$^{15}$-Gln-Leu-Ser-R$^{19}$-R$^{20}$-R$^{21}$-Leu-Leu-Gln-Asp-Ile-R$^{27}$-R$^{28}$-R$^{29}$ wherein X is H, Ac, Aqc, IAc, BrProp, For, Ibu, Nac, 2-Nac, 1- or 2-Npt, 1- or 2-Npr, PhAc, Fpr, or any other aromatic or nonpolar acyl group, $R^1$ is Tyr, His or Phe(Y), in which Y=H, F, Cl, Br, NO$_2$, NH$_2$, CH$_3$ or OCH$_3$, $R^2$ is D-Arg, D-Cit, D-Har, D-Lys, D-Tic or D-Orn, $R^3$ is Asp, D-Asp, Ala, D-Ala or Gly, $R^4$ is Ala, Abu or Gly, $R^5$ is Ile, Ala or Gly, $R^6$ is Phe, Tic, Ala, Pro, Tpi, Nal or Phe(Y), in which Y=H, F, Cl, Br, NO$_2$, NH$_2$, CH$_3$ or OCH$_3$, $R^8$ is Asn, Gin, Ser, Thr, Val, Leu, Ile, Ala, D-Ala, D-Asn, D-Gln, D-Thr, D-Leu, Abu, D-Abu, Nle, or Aib, $R^9$ is Ser $R^{10}$ is Tyr or Phe(Y), in which Y=H, F, Cl, Br, NO$_2$, CH$_3$ or OCH$_3$, $R^{11}$ is Arg, D-Arg, or Cit, $R^{12}$ is Lys, D-Lys, Cit, D-Cit, Orn, D-Orn, Nle or Ala, $R^{15}$ is Gly, Ala, Abu or Gln, $R^{19}$ is Ala or Abu, $R^{20}$ is Arg, D-Arg or Cit, $R^{21}$ is Lys, D-Lys, Orn or Cit, $R^{27}$ is Met, Nle or Abu, $R^{28}$ is Ser, Asn, Asp, Ala or Abu, $R^{29}$ is Agm, Arg-NH$_2$, Arg-OH, Cit-NH$_2$, Cit-OH, Har-NH$_2$ or Har-OH, and pharmaceutically acceptable salts thereof.

Among the preferred embodiment are peptides wherein X is PhAc or Ibu, $R^1$ is Tyr or His, $R^2$ is D-Arg or D-Cit, $R^3$ is Asp, $R^4$ is Ala, $R^5$ is Ile, $R^6$ is Phe(pCl) or Nal, $R^8$ is Asn, D-Asn, D-Thr or Abu, $R^{10}$ is Tyr or Phe(pCl), $R^{11}$ is Arg, $R^{12}$ is Lys or D-Lys, $R^{15}$ is Abu or Ala, $R^{19}$ is Ala or Abu, $R^{20}$ is Arg, $R^{21}$ is Lys, $R^{27}$ is Nle, $R^{21}$ is Ser, Asp, or Abu, $R^{29}$ is Agm or Arg-NH$_2$.

Six very preferred embodiments have the formulae:
PhAc$^0$-Tyr$^1$-D-Arg$^2$-Asp$^3$-Ala$^4$-IIe$^5$-Phe(pCl)$^6$-Thr$^7$-Asn$^8$-Ser$^9$-Tyr$^{10}$-Arg$^{11}$-Lys$^{12}$-Val$^{13}$-Leu$^{14}$-Ala$^{15}$-Gln$^{16}$Leu$^{17}$Ser$^{18}$-Ala$^{19}$Arg$^{20}$-Lys$^{21}$-Leu$^{22}$-Leu$^{23}$-Gln$^{24}$-Asp$^{25}$-Ile$^{28}$-Nle$^{27}$-Asp$^{28}$-Agm Peptide 5 PhAc$^0$-Tyr$^1$-D-Arg$^2$-Asp$^3$-Ala$^4$-Ile$^5$-Phe(pCl)$^6$-Thr$^7$-Asn$^8$-Ser$^9$-Tyr$^{10}$-Arg$^{11}$-Lys$^{12}$-Val$^{13}$-Leu$^{14}$-Abu$^{15}$-Gln$^{16}$-Leu$^{17}$-Serl$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-Ser$^{28}$-Agm Peptide 8 Ibu$^0$-Tyr$^1$-D-Arg$^2$-Asp$^3$-Ala$^4$-Ile$^5$-Phe(pCl)$^6$-Thr$^7$-Asn$^8$-Ser$^9$-Phe(pCl)$^{10}$-Arg$^{11}$-Lys$^{12}$-Val$^{13}$-Leu$^{14}$-Abu$^{15}$-Gln$^{16}$-Leu$^{17}$-Ser$^{18}$-Ala$^{19}$-Arg$^{20}$-Lys$^{21}$-Leu$^{22}$-Lru$^{23}$-Gln$^{24}$-Asp$^{26}$-Ile$^{26}$-Nle$^{27}$-Ser$^{28}$-Agm Peptide 6 PhAc$^0$-Tyr$^1$-D-Arg$^2$-Asp$^3$-Ala$^4$-Ile$^5$-Phe(pCl)$^6$-Thr$^7$-Asn$^8$-Ser$^8$-Tyr$^{10}$-Arg$^{11}$-Lys$^{12}$-Val$^{13}$-Leu$^{14}$-Ala$^{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-Ser$^{28}$-Arg$^{29}$-NH$_2$ Peptide 9 PhAc$^0$-Tyr$^1$-D-Arg$^2$-Asp$^3$-Ala$^4$-Ile$^5$-Phe(pCl)$^6$-Thr$^7$-Abu$^8$-Ser$^9$-Tyr$^{10}$-Arg$^{11}$-Lys$^{12}$-Val$^{13}$-Leu$^{14}$-Ala$^{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{26}$-Ile$^{26}$-Nle$^{27}$-Ser$^{28}$-Arg$^{29}$-NH$_2$ Peptide 11 PhAc$^0$-Tyr$^1$-D-Arg$^2$-Asp$^3$-Ala$^4$-Ile$^5$-Phe(pCl)$^6$-Thr$^7$-Abu$^8$-Ser$^9$-Tyr$^{10}$-Arg$^{11}$-Lys$^{12}$-Val$^{13}$-Leu$^{14}$-Ala$^{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-Abu$^{28}$-Arg$^{29}$-NH$_2$ Peptide 13

Under well-established convention, these may be abbreviated as follows:

[PhAc$^0$,D-Arg$^2$, Phe(pCl)$^6$, Ala$^{15}$, Nle$^{27}$, Asp$^{28}$]hGH-RH (1–28)Agm Peptide 5

[Ibu$^0$,D-Arg$^2$, Phe(pCl)$^{6,10}$, Abu$^{15}$, Nle$^{27}$]hGH-RH(1–28) Agm Peptide 6

[PhAc$^0$,D-Arg$^2$, Phe(pCl)$^6$, Abu$^{15}$, Nle$^{27}$]hGH-RH(1–28) Agm Peptide 8

[PhAc$^0$,D-Arg$^2$, Phe(pCl)$^6$, Ala$^{15}$, Nle$^{27}$]hGH-RH(1–29)-NH$_2$ Peptide 9

[PhAc$^0$,D-Arg$^2$, Phe(pCl)$^6$,Abu$^8$,Ala$^{15}$,Nle$^{27}$]hGH-RH (1–29)NH$_2$ Peptide 11

[PhAc$^0$,D-Arg$^2$, Phe(pCl)$^6$, Abu$^{8,28}$, Ala$^{15}$, Nle$^{27}$]hGH-RH (1–29)-NH$_2$ Peptide 13

β) X-A$^1$-B$^2$-A$^3$-R$^4$-R$^5$-R$^6$-Thr-A$^8$Ser-R$^{10}$-R$^{11}$-B$^{12}$-Val-Leu-R$^{15}$-A$^{16}$-A$^{17}$-Ser-R$^{19}$-B$^{20}$-B$^{21}$-Leu-Leu-Gln-A$^{26}$-Ile-R$^{27}$-R$^{28}$-B$^{29}$ wherein lactam bridge is formed between positions 1,2; 2,3; 8,12; 16,20; 17–21; 21,25; 25,29 or both 8,12 and 21,25 positions and X is H, Ac, Aqc, IAc, BrProp, For, Ibu, Nac, 2-Nac, 1- or 2-Npt, 1- or 2-Npr, PhAc, Fpr or any other aromatic or nonpolar acyl group, A is Glu, D-Glu, Gin, Asp, D-Asp, Asn, Abu, Leu, Tyr, His, Phe(Y), in which Y=H, F, Cl, Br, $NO_2$, $NH_2$, $CH_3$ or $OCH_3$, Ser, Thr, Val, lie, Ala, D-Ala, D-Asn, D-Gin, D-Thr, D-Leu, Abu, D-Abu, Nle, or Aib, B is Lys, Lys-OH, Lys-$NH_2$, D-Lys, D-Lys-OH, D-Lys-$NH_2$, Arg, Arg-OH, Arg-$NH_2$, D-Arg, D-Arg-OH, D-Arg-$NH_2$, Orn, Orn-OH, Orn-$NH_2$, D-Orn, D-Orn-OH, D-Orn-$NH_2$, Har, Har-OH, Har-$NH_2$, or Agm $R^4$ is Ala, Abu or Gly, $R^5$ is Ile, Ala or Gly, $R^6$ is Phe, Tic, Tpi, Nal or Phe(Y), in which Y=H, F, Cl, Br, $NO_2$, $NH_2$, $CH_3$ or $OCH_3$, $R^{10}$ is Tyr or Phe(Y), in which Y=H, F, Cl, Br, $NO_2$, $NH_2$, $CH_3$ or $OCH_3$, $R^{15}$ is Gly, Ala, Abu or Gln, $R^{27}$ is Met, Nle or Abu, $R^{28}$ is Ser, Asn, Asp, Ala or Abu, and pharmaceutically acceptable salts thereof.

Among the preferred embodiment are peptides wherein X is PhAc or Ibu, $A^1$ is Tyr, His, Glu, Asp or D-Asp, $B^2$ is D-Arg, D-Cit or D-Lys, $A^3$ is Asp, $R^4$ is Ala, $R^5$ is Ile, $R^6$ is Phe(pCl) or Nal, $A^8$ is Asn, D-Asn, Abu, Asp, D-Asp, Glu or D-Glu, $R^{10}$ is Tyr or Phe(4-Cl), $R^{11}$ is Arg, $B^{12}$ is Lys or D-Lys, $R^{15}$ is Abu or Ala, $A^{16}$ is Gln or Glu, $A^{17}$ is Leu or Glu, $R^{19}$ is Ala or Abu, $B^{20}$ is Arg or Lys, $B^{21}$ is Lys, $A^{25}$ is Asp or Glu, $R^{27}$ is Nle, $R^{28}$ is Ser, Asp, or Abu, $B^{29}$ is Agm, Arg-$NH_2$ or Orn-$NH_2$ and lactam bridge is formed between positions 8,12; 17,21 or both 8,12 and 21,25 positions. Five very preferred embodiments have the formulae:

cyclo$^{8,12}$[PhAc$^0$-Tyr$^1$-D-Arg$^2$-Asp$^3$-Ala$^4$-Ile$^5$-Phe(pCl)$^6$-Thr$^7$-Glu$^8$-Ser$^9$-Tyr$^{10}$-Arg$^{11}$-Lys$^{12}$-Val$^{13}$-Leu$^{14}$-Ala$^{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-Ser$^{28}$-Arg-$NH_2$ Peptide 17 cyclo$^{17,21}$[PhAc$^0$-Tyr$^1$-D-Arg$^2$-Asp$^3$-Ala$^4$-Ile$^5$-Phe(pCl)$^6$-Thr$^7$-Ser$^8$-Ser$^9$-Tyr$^{10}$-Arg$^{11}$-Lys$^{12}$-Val$^{13}$-Leu$^{14}$-Ala$^{15}$-Gln$^{16}$-Glu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-Ser$^{28}$-Arg-$NH_2$ Peptide 18 cyclo$^{8,12; 21,25}$[PhAc$^0$-Tyr$^1$-D-Arg$^2$-Asp$^3$-Ala$^4$-Ile$^5$-Phe(pCl)$^6$-Thr$^7$-Glu$^8$-Ser$^9$-Tyr$^{10}$-Arg$^{11}$-Lys$^{12}$-Val$^{13}$-Leu$^{14}$-Abu$^{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Glu$^{25}$-Ile$^{26}$-Nle$^{27}$-Ser$^{28}$-Agm Peptide 21 cyclo$^{8,12; 21,25}$[PhAc$^0$-Tyr$^1$-D-Arg$^2$-D-Asp$^3$-Ala$^4$-Ile$^5$-Phe(pCl)$^6$-Thr$^7$-Glu$^8$-Ser$^9$-Tyr$^{10}$-Arg$^{11}$-D-Lys$^{12}$-Val$^{13}$-Leu$^{14}$-Ala$^{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Glu$^{25}$-Ile$^{26}$-Nle$^{27}$-Ser$^{28}$-Arg$^{29}$-$NH_2$ Peptide 22 cyclo$^{8,12; 21,25}$[PhAc$^0$-Tyr$^1$-D-Arg$^2$-Asp$^3$-Ala$^4$-Ile$^5$-Phe(pCl)$^6$-Thr$^7$-Glu$^8$-Ser$^9$-Tyr$^{10}$-Arg$^{11}$-D-Lys$^{12}$-Val$^{13}$-Leu$^{14}$-Ala$^{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Glu$^{25}$-Ile$^{26}$-Nle$^{27}$-Ser$^{28}$-Arg$^{29}$-$NH_2$ Peptide 23

Under well-established convention, these may be abbreviated as follows:

cyclo$^{8,12}$[PhAc$^0$,D-Arg$^2$,Phe(pCl)$^6$,Glu$^8$,Ala$^{15}$,Nle$^{27}$]hGH-RH(1–29)-$NH_2$ Peptide 17 cyclo$^{17,21}$[PhAc$^0$,D-Arg$^2$,Phe(pCl)$^6$,Ser$^8$,Ala$^{15}$,Glu$^{17}$, Nle$^{27}$]hGH-RH(1–29)-$NH_2$ Peptide 18 cyclo$^{8,12; 21,25}$[PhAc$^0$,D-Arg$^2$,Phe(pCl)$^6$,Glu$^{8,25}$,Abu$^{15}$, Nle$^{27}$] hGH-RH(1–28)Agm Peptide 21 cyclo$^{8,12; 21,25}$[[PhAc$^0$,D-Arg$^2$,D-Asp$^3$,Phe(pCl)$^6$,Glu$^{8,25}$, D-Lys$^{12}$,Ala$^{15}$, Nle$^{27}$]hGH-RH(1–29)-$NH_2$ Peptide 22 cyclo$^{8,12; 21,25}$[[PhAc$^0$,D-Arg$^2$,Phe(pCl)$^6$,Glu$^{8,25}$,D-Lys$^{12}$, Ala$^{15}$,Nle$^{27}$] hGH-RH(1–29)-$NH_2$ Peptide 23

It is noted that the amino acid residues from 30 through 44 of the native GH-RH molecule do not appear to be essential to activity; nor does their identity appear to be critical. Therefore, it appears that the addition of some or all of these further amino acid residues to the C-terminus of the hGH-RH(1–29)-$NH_2$ analogues of the present invention will not affect the efficacy of these analogues as GH-RH antagonists. If some or all of these amino acids were added to the C-terminus of the hGH-RH(1–29)-$NH_2$ analogues, the added amino acid residues could be the same as residues 30 through 44 in the native hGH-RH sequence or reasonable equivalents.

Synthetic Methods.

The synthetic peptides are synthesized by a suitable method such as by exclusive solid phase techniques, by partial solid-phase techniques, by fragment condensation or by classical solution phase synthesis.

When the analogues of this invention are synthesized by solid-phase method, the C-terminus residue (here, $R^{29}$) is appropriately linked (anchored) to an inert solid support (resin) while bearing protecting groups for its alpha amino group (and, where appropriate, for its side chain functional group). After completion of this step, the alpha amino protecting group is removed from the anchored amino acid residue and the next amino acid residue, $R^{28}$, is added having its alpha amino group (as well as any appropriate side chain functional group) suitably protected, and so forth. The N-terminus protecting groups are removed after each residue is added, but the side chain protecting groups are not yet removed. After all the desired amino acids have been linked in the proper sequence, the peptide is cleaved from the support and freed from all side chain protecting group(s) under conditions that are minimally destructive towards residues in the sequence. This is be followed by a careful purification and scrupulous characterization of the synthetic product, so as to ensure that the desired structure is indeed the one obtained.

It is particularly preferred to protect the alpha amino function of the amino acids during the coupling step with an acid or base sensitive protecting group. Such protecting groups should have the properties of being stable in the conditions of peptide linkage formation, while being readily removable without destruction of the growing peptide chain and without racemization of any of the chiral centers contained therein. Suitable alpha amino protecting groups are Boc and Fmoc.

Medical Applications.

The hGH-RH antagonist peptides, or salts of these peptides, may be formulated in pharmaceutical dosage forms containing effective amounts thereof and administered to humans or animal for therapeutic or diagnostic purposes. The peptides may be used to suppress GH levels and to treat conditions associated with excessive levels of GH, e.g., diabetic retinopathy and nephropathy, and acromegaly. Also provided are methods for treating these diseases by administration of a composition of the invention to an individual needing such treatment. The main uses of GH-RH antagonists are however,in the field of cancer, for example human cancers of the breast, lung, colon, brain, and pancreas where the receptors for IGF-I are present.

DETAILED DESCRIPTION OF THE PREFERRED EMBODIMENTS

A. Abbreviations

Figure 1:
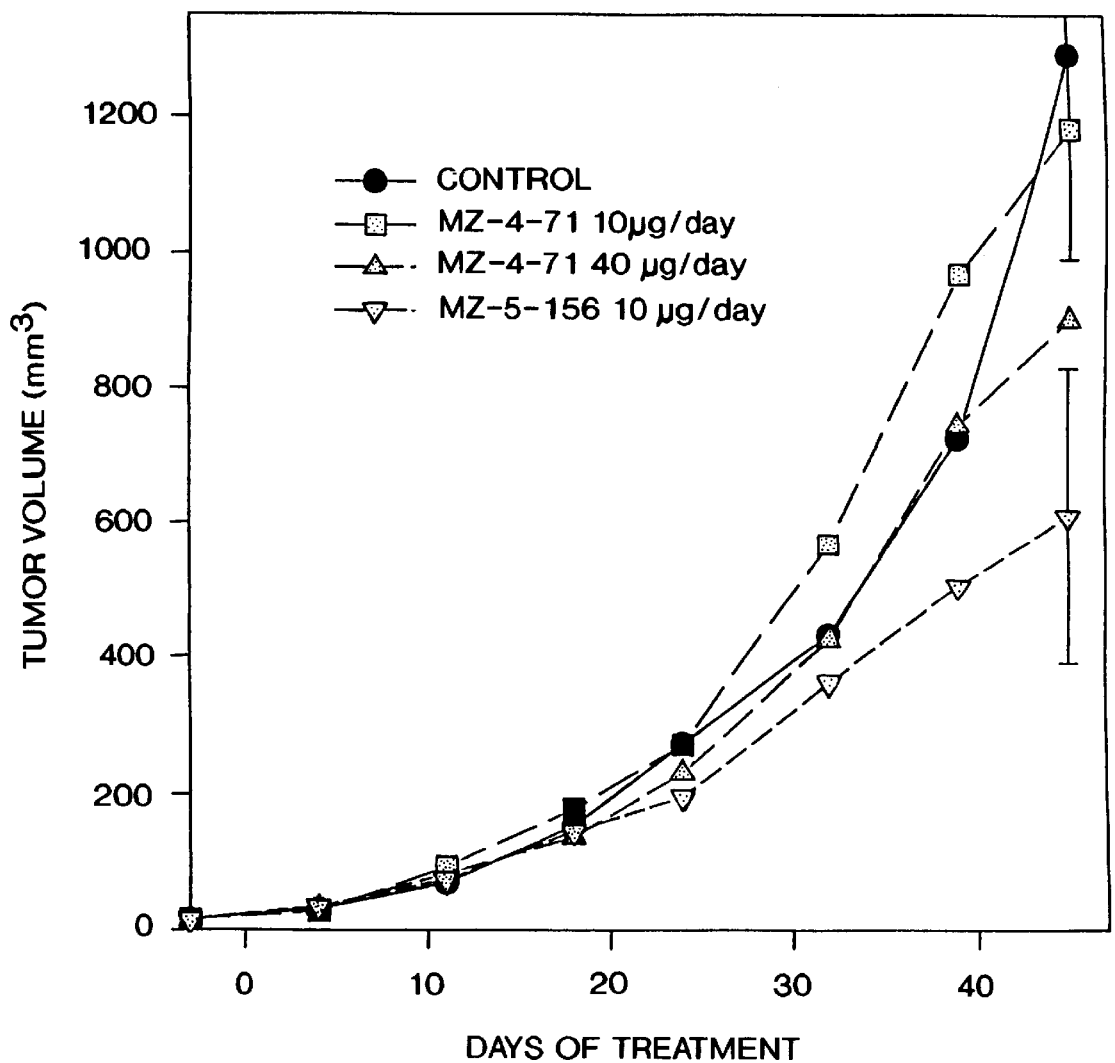
FIG. 1 is a plot of volume changes of SW 1990 human pancreatic cancers in nude mice during treatment with certain GH-RH antagonists against days of treatment.

The nomenclature used to define the peptides is that specified by the IUPAC-IUB Commissioner on Biochemical Nomenclature wherein, in accordance with conventional representation, the amino group at the N-terminus appears to the left and the carboxyl group at the C-terminus appears to the right. The term "natural amino acid" as used herein means one of the common, naturally occurring L-amino acids found in naturally occurring proteins: Gly, Ala, Val, Leu, Ile, Ser, Thr, Lys, Arg, Asp, Asn, Glu, Gln, Cys, Met Phe, Tyr, Pro, Trp and His. When the natural amino acid residue has isomeric forms, it is the L-form of the amino acid that is represented herein unless otherwise expressly indicated.

Non-coded amino acids, or amino acid analogues, are also incorporated into the GH-RH antagonists. ("Non-coded" amino acids are those amino acids which are not among the approximately 20 natural amino acids found in naturally occurring peptides.) Among the non-coded amino acids or amino acid analogues which may be used in the hGH-RH antagonist peptides are the following: by Abu is meant alpha amino butyric acid, by Agm is meant agmatine (1-amino-4-guanidino-butane), by Aib meant alpha amino isobutyric acid, by Har is meant homoarginine, by Nal is meant 2-naphthyl-alanine, by Nle is meant norleucine, and by Tic is meant 1,2,3,4-tetrahydroisoquinoline carboxilic acid. When these non-coded amino acids, or amino acid analogues, have isomeric forms, it is the L-form of the amino acid that is represented unless otherwise expressly indicated.

Abbreviations used herein are:

| | |
|---|---|
| Abu | α-aminobutyric acid |
| Ac | acetyl |
| AcOH | acetic acid |
| $Ac_2O$ | acetic anhydride |
| Agm | agmatine (1-amino-4-guanidino-butane) |
| Aib | α-aminoisobutyric acid |
| Aqc | anthraquinone-2-carbonyl |
| BHA | benzhydrylamine |
| Boc | tert.butyloxycarbonyl |
| BOP | benzotriazole-1-yl-oxy-tris-(dimethylamino)-phosphonium hexafluorophosphate |
| BrProp | bromopropionyl |
| cHx | cyclohexyl |
| Cit | citrulline (2-amino-5-ureidovaleric acid) |
| DCM | dichloromethane |
| DIC | N,N'-diisopropylcarbodiimide |
| DIEA | diisopropylethylamine |
| DMF | dimethylformamide |
| Fpr | phenylpropionyl |
| GH | growth hormone |
| GH-RH | GH releasing hormone |
| Har | homoarginine |
| HBTU | 2-(1H-Benzotriazol-1-yl)-1,1,3,3-tetramethyluronium hexaflourophosphate |
| hGH-RH | human GH-RH |
| HOBt | 1-hydroxybenzotriazole |
| HPLC | high performance liquid chromatography |
| IAc | iodoacetyl |
| Ibu | isobutyryl |
| MeOH | methanol |
| MeCN | acetonitrile |
| MBHA | para-methylbenzhydrylamine |
| Nac | 1-naphthylacetyl |
| 2-Nac | 2-naphthylacetyl |
| Nal | 2-naphthylalanine |
| NMM | N-methylmorpholine |
| Npr | naphthylpropionyl |
| Npt | naphthoyl |
| Phe(pCl) | para-chloro-phenylalanine |
| PhAc | phenylacetyl |
| rGH-RH | rat GH-RH |
| RP-HPLC | reversed phase HPLC |
| SPA | sulfophenoxy |
| TFA | trifluoroacetic acid |
| Tic | 1,2,3,4-tetrahydroisoquinoline |
| Tos | para-toluenesulfonyl |
| Tpi | 2,3,4,9-tetrahydro-1H-pyrido[3,4-b]indol-3-carboxylic acid |
| Tyr(Me) | tyrosine methylether |
| Z | benzyloxycarbonyl |

B. The GH-RH Analogues

The hGH-RH analogues of the present invention were designed to increase the affinities of the peptides to the receptor, to improve metabolic stability and to maximize the amphiphilic secondary structure of the molecules. Many of these analogues cause very effective and long lasting inhibition of the GH release stimulated by hGH-RH$(1-29)NH_2$ in vitro and in vivo.

The following embodiments are specially preferred as having remarkable bioactivity:

[Ibu$^0$,D-Arg$^2$,Phe(pCl)$^6$,Abu$^{15}$,Nle$^{27}$,Cit$^{29}$]hGH-RH (1–29)-NH$_2$ Peptide # 1

[Ibu$^0$,D-Arg$^2$,Phe(pCl)$^6$,Abu$^{8,15}$,Nle$^{27}$,Cit$^{29}$]hGH-RH (1–29)-NH$_2$ Peptide # 2

[PhAc$^0$,D-Arg$^2$,Phe(pCl)$^6$,Abu$^{8,15}$,Nle$^{27}$,Cit$^{29}$]hGH-RH (1–29)-NH$_2$ Peptide # 3

[Ac-Nal$^0$,D-Arg$^2$,Phe(pCl)$^6$,Abu$^{15}$,Nle$^{27}$]hGH-RH(1–28) Agm Peptide # 4

[PhAc$^0$,D-Arg$^2$,Phe(pCl)$^6$,Ala$^{15}$,Nle$^{27}$,Asp$^{28}$]hGH-RH (1–28)Agm Peptide # 5

[Ibu$^0$,D-Arg$^2$,Phe(pCl)$^{6,10}$,Abu$^{15}$,Nle$^{27}$]hGH-RH(1–28) Agm Peptide # 6

[Ibu$^0$,D-Arg$^2$,Phe(pCl)$^6$,D-Thr$^8$,Abu$^{15}$,Nle$^{27}$]hGH-RH (1–28)Agm Peptide # 7

[PhAc$^0$,D-Arg$^2$,Phe(pCl)$^6$,Abu$^{15}$,Nle$^{27}$]hGH-RH(1–28) Agm Peptide # 8

[PhAc$^0$,D-Arg$^2$,Phe(pCl)$^6$,Ala$^{15}$,Nle$^{27}$]hGH-RH(1–29)-NH$_2$ Peptide # 9

[PhAc$^0$,Tyr(Me),D-Arg$^2$,Phe(pCl)$^6$,Ala$^{15}$,Nle$^{27}$]hGH-RH (1–29)-NH$_2$ Peptide # 10

[PhAc$^0$,D-Arg$^2$,Phe(pCl)$^6$,Abu$^8$,Ala$^{15}$,Nle$^{27}$],hGH-RH (1–29)NH$_2$ Peptide # 11

[PhAc$^0$,D-Arg$^2$,Nal$^6$,Abu$^{8,28}$,Ala$^{15}$,Nle$^{27}$]hGH-RH(1–29) NH$_2$ Peptide # 12

[PhAc$^0$,D-Arg$^2$,Phe(pCl)$^6$,Abu$^{8,28}$,Ala$^{15}$,Nle$^{27}$]hGH-RH (1–29)NH$_2$ Peptide # 13

[PhAc$^0$,D-Arg$^2$,Phe(pCl)$^6$,Abu$^8$,D-Lys$^{12}$,Ala$^{15}$,Nle$^{27}$]hGH-RH(1–29)NH$_2$ Peptide # 14

[PhAc$^0$,D-Arg$^2$,Phe(pCl)$^6$,Orn$^{12,21}$,Abu$^{15}$,Nle$^{27}$]hGH-RH (1–28)Agm Peptide # 15

[Ibu$^0$,D-Arg$^2$,Phe(pCl)$^6$,Orn$^{12,21}$,Abu$^{15}$,Nle$^{27}$]hGH-RH (1–28)Agm Peptide # 16 cyclo$^{8,12}$[PhAc$^0$,D-Arg$^2$,Phe(pCl)$^6$,Glu$^8$,Ala$^{15}$,Nle$^{27}$]hGH-RH(1–29)NH$_2$ Peptide # 17 cyclo$^{17,21}$[PhAc$^0$,D-Arg$^2$,Phe(pCl)$^6$,Ser$^8$,Ala$^{15}$,Glu$^{17}$, Nle$^{27}$]hGH-RH(1–29)NH$_2$ Peptide # 18 cyclo$^{25,29}$[PhAc$^0$,D-Arg$^2$,Phe(pCl)$^6$,Abu$^8$,Ala$^{15}$,D-Asp$^{25}$, Nle$^{27}$,Orn$^{29}$]hGH-RH(1–29)NH$_2$ Peptide # 19 cyclo$^{25,29}$[PhAc$^0$,D-Arg$^2$,Nal$^6$,Abu$^8$,Ala$^{15}$,D-Asp$^{25}$,Nle$^{27}$, Orn$^{29}$]hGH-RH(1–29)NH$_2$ Peptide # 20 cyclo$^{8,12;21,25}$[PhAc$^0$,D-Arg$^2$,Phe(pCl)$^6$,Glu$^{8,25}$,Abu$^{15}$, Nle$^{27}$]hGH-RH(1–28)Agm Peptide # 21 cyclo$^{8,12;21,25}$[phAc$^0$,D-Arg$^2$,D-Asp$^3$,Phe(pCl)$^6$,Glu$^{8,25}$,D-Lys$^{12}$,Ala$^{15}$,Glu$^{25}$,Nle$^{27}$,hGH-RH(1–29)NH$_2$ Peptide # 22 cyclo$^{8,12;21,25}$,PhAc$^0$,D-Arg$^2$,Phe(pCl)$^6$,Glu$^{8,25}$,D-Lys$^{12}$, Ala$^{25}$,Nle$^{27}$]hGH-RH(1–29)NH$_2$ Peptide # 23
cyclo$^{8,12;21,25}$[PhAc$^0$,D-Arg$^2$,Phe(pCl)$^6$,Asp$^8$,D-Lys$^{12}$, Ala$^{15}$,Glu$^{25}$,Nle$^{27}$]hGH-RH(1–29)NH$_2$ Peptide # 24
[PhAc$^0$,D-Arg$^2$,Tic$^6$,Abu$^{15}$,Nle$^{27}$]hGH-RH(1–28)Agm Peptide # 25
[PhAc$^0$,D-Tic$^2$,Phe(pCl)$^6$,Abu$^{15}$,Nle$^{27}$]hGH-RH(1–28) Agm Peptide # 26

C. Method of Preparation

1. Overview of Synthesis

The peptides are synthesized by a suitable method such as by exclusive solid phase techniques, by partial solid-phase techniques, by fragment condensation or by classical solution phase synthesis. For example, the techniques of exclusive solid-phase synthesis are set forth in the textbook "Solid Phase Peptide Synthesis", J. M. Stewart and J. D. Young, Pierce Chem. Company, Rockford, 111, 1984 (2nd. ed.), and M. Bodanszky, "Principles of Peptide Synthesis", SpringerVerlag, 1984. The hGH-RH antagonist peptides are preferably prepared using solid phase synthesis, such as that generally described by Merrifield, J.Am.Chem.Soc., 85, p. 2149 (1963), although other equivalent chemical syntheses known in the art can also be used as previously mentioned.

The synthesis is carried out with amino acids that are protected at their alpha amino group. Urethane type protecting groups (Boc or Fmoc) are preferably used for the protection of the alpha amino group. The preferred protecting group is Boc.

In solid phase synthesis, the N-alpha-protected amino acid moiety which forms the aminoacyl group of the final peptide at the C-terminus is attached to a polymeric resin support via a chemical link. After completion of the coupling reaction, the alpha amino protecting group is selectively removed to allow subsequent coupling reactions to take place at the amino-terminus, preferably with 50% TFA in DCM when the N-alpha-protecting group is Boc. The remaining amino acids with similarly Boc-protected alpha amino groups are coupled stepwise to the free amino group of the preceding amino acid on the resin to obtain the desired peptide sequence. Because the amino acid residues are coupled to the alpha amino group of the C-terminus residue, growth of the synthetic hGH-RH analogue peptides begins at the C terminus and progresses toward the N-terminus. When the desired sequence has been obtained, the peptide is acylated, if appropriate, and it is removed from the support polymer.

Each protected amino acid is used in excess (2.5 or 3 equivalents) and the coupling reactions are usually carried out in DCM, DMF or mixtures thereof. The extent of completion of the coupling reaction is monitored at each stage by the ninhydrin reaction. In cases where incomplete coupling is determined, the coupling procedure is repeated before removal of the alpha amino protecting group prior to the coupling of the next amino acid.

A typical synthesis cycle is shown in Table I.

TABLE I

Protocol for a Typical Synthetic Cycle Using Boc-strategy

| Step | Reagent | Mixing Time (min) |
|---|---|---|
| 1. Deprotection | 50% TFA in DCM | 5 + 25 |
|  | DCM wash | 1 |
|  | 2-propanol wash | 1 |

TABLE I-continued

Protocol for a Typical Synthetic Cycle Using Boc-strategy

| Step | Reagent | Mixing Time (min) |
|---|---|---|
| 2. Neutralization | 5% DIEA in DCM | 1 |
|  | DCM wash | 1 |
|  | MeOH wash | 1 |
|  | 5% DIEA in DCM | 3 |
|  | MeOH wash | 1 |
|  | DCM wash (3 times) | 1–1 |
| 3. Coupling | 3 equiv. Boc-amino acid in DCM or DMF + 3 equiv. DIC or the preformed |  |
|  | HOBt ester of the Boc-amino acid | 60 |
|  | MeOH wash | 2 |
|  | DCM wash | 2 |
| 4. Acetylation (if appropriate) | Ac$_2$O in DCM (30%) | 10 + 20 |
|  | MeOH wash (3 times) | 2 |
|  | DCM wash (3 times) | 2 |

After completion of the synthesis, the cleavage of the peptide from the resin can be effected using procedures well known in peptide chemistry.

Some of the amino acid residues of the peptides have side chain functional groups which are reactive with reagents used in coupling or deprotection. When such side chain groups are present, suitable protecting groups are joined to these functional groups to prevent from undesirable chemical reactions occurring during the reactions used to form the peptides. The following general rules are followed in selecting a particular side chain protecting group: (a) the protecting group preferably retains its protecting properties and is not split off under coupling conditions, (b) the protecting group should be stable in conditions for removing the alpha amino protecting group at each step of the synthesis, (c) the side chain protecting group must be removable upon the completion of the synthesis of the desired amino acid sequence, under reaction conditions that will not undesirably alter the peptide chain.

The initial synthetic steps utilized herein are disclosed in U.S. Pat. No. 4,914,189 which is incorporated by reference herein. Reference is particularly made to Examples I through IV therein.

The reactive side chain functional groups are preferably protected as follows: benzyl for Thr and Ser; 2,6-dichlorobenzyloxycarbonyl for Tyr; p-toluene-sulfonyl for Arg; 2-chlorobenzyloxycarbonyl or fluorenylmethyloxy carbonyl for Lys, Orn; and cyclohexyl or fluorenylmethyl for Asp and Glu. The side chains of Asn and Gln are unprotected.

2. Coupling R$^{29}$ to the support Polymer

The hGH-RH antagonist peptides may be synthesized on a variety of support polymers. These support polymers may be amino resins such as amino-methyl resins, benzhydrylamine resins, p-methylbenzhydrylamine resins and the like. Boc-R$^{29}$ is the initial material joined to the support phase, suitably Boc-Arg(Tos)-OH or Boc-Agm.

For the synthesis of peptides having Agm at the C-terminus, it is preferred that the support phase [SP] is an amino methyl resin. The guanidino group of Boc-Agm is joined to the support polymer via a stable but readily cleavable bridging group. It has been found that such a bridge may be readily provided by the sulfonyl phenoxy acetyl moiety. The alpha amino Boc-protected Agm is reacted with the chlorosulfonyl phenoxy acetic acid

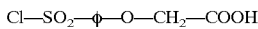

to form

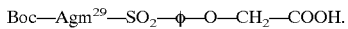

This compound is then coupled to the support polymer [SP] using DIC or BOP as activating reagent to yield:

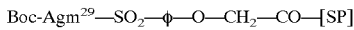

For the synthesis of peptides having Arg-NH$_2$ at the C-terminus, Boc-Arg(Tos)—OH is coupled to the neutralized BHA or MBHA resin using DIC or BOP as activating reagent.

3. Stepwise Coupling of Amino Acid Residues.

Utilizing the Boc-protected Agm resin (California Peptide Res. Inc.), (or the Boc-Arg(Tos)-resin), the peptide itself may suitably be built up by solid phase synthesis in the conventional manner. The selection of an appropriate coupling reagent is within the skill of the art. Particularly suitable as coupling reagents are N,N'-diisopropyl carbodiimide (DIC) or the BOP carboxyl activating reagent.

Each protected amino acid is coupled in about a three-fold molar excess, with respect to resin-bound aminoacyl residue(s), and the coupling may be carried out in a medium such as DMF: $CH_2Cl_2$ (1:1) or in DMF or $CH_2Cl_2$ alone. In cases where incomplete coupling occurs, the coupling procedure is repeated before removal of the alpha amino protecting group. The success of the coupling reaction at each stage of the synthesis is preferably monitored by the ninhydrin reaction.

In case of lactam bridge formation, the side-chain protecting groups (Fmoc and OFm) of Lys or Orn and Asp or Glu respectively of the Boc-protected peptide-resin are selectively removed with 20% piperidine in DMF. Formation of lactam bridge is achieved on the solid support using HBTU coupling agent.

4. Removal of the Peptide from the Support Polymer.

When the synthesis is complete, the peptide is cleaved from the support phase. Removal of the peptide from the resin is performed by treatment with a reagent such as liquid hydrogen fluoride which also cleaves all remaining side chain protecting groups.

Suitably, the dried and protected peptide-resin is treated with a mixture consisting of 1.0 mL m-cresol and 10 mL anhydrous hydrogen fluoride per gram of peptide-resin for 60 min at 0° C. to cleave the peptide from the resin as well as to remove all side chain protecting groups. After the removal of the hydrogen fluoride under a stream of nitrogen and vacuum, the free peptides are precipitated with ether, filtered, washed with ether and ethyl acetate, extracted with 50% acetic acid, and lyophilized.

5. Purification

The purification of the crude peptides can be effected using procedures well known in peptide chemistry. For example, purification may be performed on a MacRabbit HPLC system (Rainin Instrument Co. Inc., Woburn, Mass.) with a Knauer UV Photometer and a Kipp and Zonen BD40 Recorder using a 10×250 mm VYDAC 228TP column packed with C8 silica gel (300 Å pore size, 10 μm particle size) (Rainin Inc.) The column is eluted with a solvent system consisting of (A) 0.1% aqueous TFA and (B) 0.1% TFA in 70% aqueous MeCN in a linear gradient mode (e.g., 30–65% B in 120 min). The eluent is monitored at 220 nm, and fractions are examined by analytical HPLC using a Hewlett-Packard Model HP-1090 liquid chromatograph and pooled to give maximum purity. Analytical HPLC is carried out on a W-Porex C18 reversed-phase column (4.6×250 mm, 5 μm particle size, 300 Å pore size) (Phenomenex, Rancho Palos Verdes, Calif.) using isocratic elution with a solvent system consisting of (A) and (B) defined above. The peaks are monitored at 220 and 280 nm. The peptides are judged to be substantially (>95%) pure by analytical HPLC. The expected amino acid composition is also confirmed by amino acid analysis.

D. Pharmaceutical Composition

The peptides of the invention may be administered in the form of pharmaceutically acceptable, nontoxic salts, such as acid addition salts. Illustrative of such acid addition salts are hydrochloride, hydrobromide, sulphate, phosphate, fumarate, gluconate, tannate, maleate, acetate, citrate, benzoate, succinate, alginate, pamoate, malate, ascorbate, tartarate, and the like. Particularly preferred antagonists are salts of low solubility, e.g., pamoate salts and the like. These exhibit long duration of activity.

The compounds of the present invention are suitably administered to subject humans or animals s.c., i.m., or i.v; intranasally or by pulmonary inhalation; or in a depot form (e.g., microcapsules, microgranules, or cylindrical rod like implants) formulated from a biodegradable suitable polymer (such as D,L-lactide-coglycolide), the former two depot modes being preferred. Other equivalent modes of administration are also within the scope of this invention, i.e., continuous drip, depot injections, infusion pump and time release modes such as microcapsules and the like. Administration is in any physiologically acceptable injectable carrier, physiological saline being acceptable, though other carriers known to the art may also be used.

The peptides are preferably administered parenterally, intramuscularly, subcutaneously or intravenously with a pharmaceutically acceptable carrier such as isotonic saline. Alternatively, the peptides may be administered as an intranasal spray with an appropriate carrier or by pulmonary inhalation. One suitable route of administration is a depot form formulated from a biodegradable suitable polymer, e.g., poly-D,L-lactide-coglycolide as microcapsules, microgranules or cylindrical implants containing dispersed antagonistic compounds.

The amount of peptide needed depends on the mode of administration and the intended result. In general, the dosage range is between 1–100 μg/kg of body weight of the host per day.

E. Therapeutic Uses of GH-RH Antagonists hGH-RH antagonists can be used in treatment of conditions caused by excess growth hormone, for example acromegaly, which is manifested by an abnormal enlargement of the bones of the face and extremities. The GH-RH antagonists may also be used to treat diabetic nephropathy (the main cause of blindness in diabetics) and diabetic retinopathy, in which damage to the eye and kidney respectively is thought to be due to GH.

The hGH-RH antagonists are designed to block the binding and therefore the action of GH-RH, which stimulates the secretion of GH, which in turn stimulates production of IGF I. GH-RH antagonists may be administered alone or together with somatostatin analogues, a combination which more completely suppresses IGF-I levels. It is advantageous to administer antagonists of GH-RH rather than somatostatin due to the fact that GH-RH antagonists may be utilized in situations where target sites do not have somatostatin receptors.

However, the main applications of GH-RH antagonists are in the field of cancer. This is based on the following considerations: GH-RH antagonists are designed to block the binding and therefore the action of GH-RH, which stimulates the secretion of GH, which in turn stimulates production of insulin-like growth factor I (IGF-I) also called somatomedin-C. The involvement of IGF-I (somatomedin-C) in breast cancer, prostate cancer, colon cancer, bone tumors and other malignancies is well established, and somatostatin analogues alone do not adequately suppress GH and IGF-I levels. A complete suppression of IGF-I levels or secretion is required for a better inhibition of tumor growth. Autocrine production of IGF-I by various tumors could be also under control of GH-RH and might therefore be inhibited by GH-RH antagonists. GH-RH antagonists might also inhibit the production of IGF-I. A more detailed theoretical background of the applications of GH-RH in the field of oncology (cancer) is as follows: The receptors for IGF-I are present in primary human breast cancers, in lung cancers, in human colon cancers, in human brain tumors, and in human pancreatic cancers.

The presence of IGF-I receptors in these tumors appears to be related to malignant transformation and proliferations of these cancers. IGF-I can act as endocrine, paracrine or autocrine growth factor for various human cancers, that is the growth of these neoplasms is dependent on IGF-I. GH-RH antagonists by suppressing GH secretion would lower the production of IGF-I. Since IGF-I stimulates growth of these various neoplasms (cancers), the lowering of circulating IGF-I levels should lead to tumor growth inhibition. It is possible that GH-RH antagonists could also lower paracrine or autocrine production of IGF-I by the tumors, which should also lead to inhibition of cancer proliferation. These views are in accordance with modern concepts of clinical oncology. GH-RH antagonists should be given alone or together with somatostatin analogues and a combination would achieve a more complete suppression of IGF-I levels, elimination of tissue IGF-I levels, e.g., in human osteosarcomas, as well as breast cancer, colon cancer, prostate cancer, and non-small cell lung cancer (non-SCLC).

The advantage of GH-RH antagonists over somatostatin analogues is based on the fact that GH-RH antagonists may be utilized for suppression of tumors which do not have somatostatin receptors, for example human osteogenic sarcomas.

The present invention is described in connection with the following examples which are set forth for the purposes of illustration only. In the examples, optically active protected amino acids in the L-configuration are used except where specifically noted.

The following Examples set forth suitable methods of synthesizing the novel GH-RH antagonists by the solid-phase technique.

EXAMPLE I
Synthesis of Boc-agmatine

EXAMPLE II
Synthesis of 4-Chlorosulfonyl Phenoxyacetic Acid (Cl-SPA)

EXAMPLE III
Boc-agmatine-[SPA]

EXAMPLE IV
Coupling of Boc-agmatine-[SPA] to Support Phase

The initial synthetic sequence utilized herein and indicated by headings above is disclosed in Examples I through IV of U.S. Pat. No. 4,914,189, which Examples are incorporated herein by reference.

EXAMPLE V

Ibu-Tyr$^1$-D-Arg$^2$-Asp$^3$-Ala$^4$-Ile$^5$-Phe(pCl)$^6$-Thr$^7$-Asn$^8$-Ser$^9$-Tyr$^{10}$-Arg$^{11}$-Lys$^{12}$-Val$^{13}$-Leu$^{14}$-Abu$^{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-Ser$^{28}$-Cit$^{29}$-NH$_2$ (Peptide 1)
([Ibu$^0$,D-Arg$^2$,Phe(pCl)$^6$,Abu$^{15}$,Nle$^{27}$,Cit$^{29}$]hGH-RH(1–29)NH$_2$)

The synthesisis is conducted in a stepwise manner using manual solid phase peptide synthesis equipment. Briefly, benzhydrylamine (BHA) resin (Bachem, Calif.) (100 mg, 0.044 mmole) is neutralized with 5% DIEA in CH$_2$Cl$_2$ and washed according to the protocol described in Table 1. The solution of Boc-Cit-OH (61mg, 0.25 mmole) in DMF-CH$_2$Cl$_2$ (1:1) is shaken with the neutralized resin and DIC (44 µL, 0.275 mmole) in a manual solid phase peptide synthesis equipment for 1 hour. After the completion of the coupling reaction is proved by negative ninhydrin test, deprotection with 50% TFA in CH$_2$Cl$_2$, and neutralization with 5% DIEA in CH$_2$Cl$_2$, the peptide chain is built stepwise by coupling the following protected amino acids in the indicated order on the resin to obtain the desired peptide sequence: Boc-Ser (Bzl)-OH, Boc-Nle-OH, Boc-Ile-OH, Boc-Asp(OcHx)-OH, Boc-Gln-OH, Boc-Leu-OH, Boc-Leu-OH, Boc-Lys(2-Cl-Z)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2-Cl-Z)-OH, Boc-Arg(Tos)-OH, Boc-Tyr(2,6-diCl-Z)-OH, Boc-Ser(Bzl)-OH, Boc-Asn-OH, Boc-Thr(Bzl)-OH, Boc-Phe(pCl)-OH, Boc-Ile-OH, Boc-Ala-OH, Boc-Asp(OcHx)-OH, Boc-D-Arg(Tos)-OH, Boc-Tyr(2,6-diCl-Z)-OH.

These protected amino acid residues (also commonly available from Bachem Co.) are represented above according to a well accepted convention. The suitable protecting group for the side chain functional group of particular amino acids appears in parentheses. The OH groups in the above formulae indicate that each residue's carboxyl terminus is free.

The protected amino acids (0.25 mmole each) are coupled with DIC (44 µL, 0.275 mmole) with the exceptions of Boc-Asn-OH and Boc-Gln-OH which are coupled with their preformed HOBt esters. After removal of the N$^\alpha$-Boc protecting group from Tyr$^1$, the peptide is acylated with isobutyric acid (Ibu) (75 mg, 0.4 mmole) using DIC (70 µL, 0.44 mmole).

In order to cleave the peptide from the resin and deprotect it, the dried peptide resin (138 mg) is stirred with 0.5 mL m-cresol and 5 mL hydrogen fluoride (HF) at 0° C. for 1 hour. After evaporation of the HF under vacuum, the remnant is washed with dry diethyl ether and ethyl acetate. The cleaved and deprotected peptide is dissolved in 50% acetic acid and separated from the resin by filtration. After dilution with water and lyophilization, 34 mg crude product is obtained.

The crude peptide is checked by analytical HPLC using a Hewlett-Packard Model HP-1090 liquid chromatograph with a W-Porex C18 reversed-phase column (4.6×250 mm, 5 µm particle size, 300 Å pore size from Phenomenex, Rancho Palos Verdes, Calif.) and linear gradient elution, (e.g., 40–70% B) with a solvent system consisting of (A) 0.1% aqueous TFA and (B) 0.1% TFA in 70% aqueous MeCN. 34 mg of the crude peptide is dissolved in AcOH/H$_2$O, stirred, filtered and applied on a VYDAC 228TP column (10×250 mm) packed with C8 silica gel. The column is eluted with a solvent system described above in a linear gradient mode (e.g., 30–55% B in 120 min); flow rate 2 mL/min. The eluent is monitored at 220 nm, and fractions are examined by analytical HPLC. Fractions with purity higher than 95% are pooled and lyophilized to give 1.2 mg pure product. The analytical HPLC is carried out on a W-Porex C18 reversed-phase column described above using isocratic elution with a solvent system described above with a flow rate of 1.2 mL/min. The peaks are monitored at 220 and 280 nm. The product is judged to be substantially (>95%) pure by analytical HPLC. The expected amino acid composition is also confirmed by amino acid analysis.

Peptides 2 and 3 are synthesized in the same manner as Peptide 1, except that Boc-Asn-OH$^8$ is replaced with Boc-Abu-OH (0.25 mmole) and the resulting peptides are acylated with isobutyric acid or phenylacetic acid repectively, to yield:

[Ibu$^0$,D-Arg$^2$,Phe(pCl)$^6$,Abu$^{8,15}$,Nle$^{27}$,Cit$^{29}$]hGH-RH (1–29)-NH$_2$ Peptide # 2

[PhAc$^0$,D-Arg$^2$,Phe(pCl)$^6$,Abu$^{8,15}$,Nle$^{27}$,Cit$^{29}$]hGH-RH (1–29)-NH$_2$ Peptide # 3

EXAMPLE VI

PhAc$^0$-Tyr$^1$-D-Arg$^2$-Asp$^3$-Ala$^4$-Ile$^5$-Phe(pCl)$^6$-Thr$^7$-Asn$^8$-Ser$^9$-Tyr$^{10}$-Arg$^{11}$-Lys$^{12}$-Val$^{13}$-Leu$^{14}$-Abu$^{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$Asp$^{25}$-Ile$^{26}$-Nle$^{27}$-Ser$^{28}$-Agm$^{29}$ (Peptide 8)

or [PhAc$^0$,D-Arg$^2$, Phe(pCl)$^6$,Abu$^{15}$,Nle$^{27}$]hGH-RH(1–28) Agm

The synthesisis is conducted in a stepwise manner using manual solid phase peptide synthesis equipment. Briefly, Boc-Agm-SPA-aminomethyl resin (California Peptide Research Co., Inc., California) (200 mg, 0.06 mmole) is deprotected with 50% TFA in CH$_2$Cl$_2$, neutralized with 5% DIEA in CH$_2$Cl$_2$, and washed as described in Table 1. The solution of Boc-Ser(Bzl)-OH (55 mg, 0.18 mmole) in DMF-CH$_2$Cl$_2$ (1:1) is shaken with the H-Agm-SPA-aminomethyl resin and DIC (31 μL, 0.2 mmole) in a manual solid phase peptide synthesis equipment for 1 hour. After the completion of the coupling reaction is proved by negative ninhydrin test, deprotection with 50% TFA in CH$_2$Cl$_2$ and neutralization with 5% DIEA in CH$_2$Cl$^2$, and washed as described in Table I to build the peptide chain step-wise by coupling the following protected amino acids in the indicated order on the resin: Boc-Nle-OH, Boc-Ile-OH, Boc-Asp(OcHx)-OH, Boc-Gln-OH, Boc-Leu-OH, Boc-Leu-OH, Boc-Lys(2-Cl-Z)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2-Cl-Z)-OH, Boc-Arg(Tos)-OH, Boc-Tyr (2,6-diCl-Z)-OH, Boc-Ser(Bzl)-OH, Boc-Asn-OH, Boc-Thr (Bzl)-OH, Boc-Phe(pCl)-OH, Boc-Ile-OH, Boc-Ala-OH, Boc-Asp (OcHx)-OH, Boc-D-Arg(Tos)-OH and Boc-Tyr(2,6-diCl-Z)-OH.

The protected amino acids (0.18 mmole each) are coupled with DIC (31 μL, 0.2 mmole) with the exceptions of Boc-Asn-OH and Boc-Gln-OH which are coupled with their preformed HOBt esters. After removal of the N$^\alpha$-Boc protecting group from Tyr$^1$, the peptide is acylated with phenylacetic acid (66 mg, 0.5 mmole) using DIC (88 μL, 0.55 mmole) as coupling agent.

In order to cleave the peptide from the resin and deprotect it, the dried peptide resin (148 mg) is stirred with 0.5 mL m-cresol and 5 mL hydrogen fluoride (HF) at 0° C. for 1 hour. After evaporation of the HF under vacuum, the remnant is washed with dry diethyl ether and ethyl acetate. The cleaved and deprotected peptide is dissolved in 50% acetic acid and separated from the resin by filtration. After dilution with water and lyophilization, 62 mg crude product is obtained.

62 mg of the GH-RH antagonist peptide is dissolved in AcOH/H$_2$O and purified by RP-HPLC using the same procedure and equipments described in Example V. The product is judged to be substantially (>95%) pure by analytical HPLC. Confirmation of the structure is provided by amino acid analysis.

Peptides 4, 5, 6, 7, 15, 16, 25 and 26 are synthesized in the same manner as Peptide 1, except that these peptides also contain other substitutions, to yield:

Ac-Nal$^0$,D-Arg$^2$,Phe(pCl)$^6$,Abu$^{15}$,Nle$^{27}$]hGH-RH(1–28) Agm Peptide # 4

[PhAc$^0$,D-Arg$^2$,Phe(pCl)$^6$,Ala$^{15}$,Nle$^{27}$,Asp$^{28}$]hGH-RH (1–28)Agm Peptide 5

[Ibu$^0$,D-Arg$^2$,Phe(pCl)$^{6,10}$,Abu$^{15}$,Nle$^{27}$]hGH-RH(1–28) Agm Peptide # 6

[Ibu$^0$,D-Arg$^2$,Phe(pCl)$^6$,D-Thr$^8$,Abu$^{15}$,Nle$^{27}$]hGH-RH (1–28)Agm Peptide 7

[PhAc$^0$,D-Arg$^2$,Phe(pCl)$^6$,Orn$^{12,21}$,Abu$^{15}$,Nle$^{27}$]hGH-RH (1–28)Agm Peptide 15

[Ibu$^0$,D-Arg$^2$,Phe(pCl)$^6$,Orn$^{12,21}$,Abu$^{15}$,Nle$^{27}$]hGH-RH (1–28)Agm Peptide 16

[PhAc$^0$,D-Arg$^2$,Tic$^6$,Abu$^{15}$,Nle$^{27}$) hGH-RH (1–28)Agm Peptide 25

[PhAc$^0$,D-Tic$^2$,Phe(pCl)$^6$,Abu$^{15}$,Nle$^{27}$)]hGH-RH (1–28) Agm Peptide 26

EXAMPLE VII

PhAc-Tyr$^1$-D-Arg$^2$-Asp$^3$-Ala$^4$-Ile$^5$-Phe(pCl)$^6$-Thr$^7$-Asn$^8$-Ser$^9$-Tyr$^{10}$-Arg$^{11}$-Lys$^{12}$-Val$^{13}$-Leu$^{14}$-Ala$^{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-Ser$^{28}$-Arg$^{29}$-NH$_2$ (Peptide 9)

or [PhAco$^0$,D-Arg$^2$,Phe(pCel)$^6$,Ala$^{15}$,Nle$^{27}$]hGH-RH (1–29)NH$_2$

The synthesis is conducted in a stepwise manner using manual solid phase peptide synthesis equipment. Briefly, benzhydrylamine (BHA) resin (Bachem, Calif.) (100 mg, 0.044 mmole) is neutralized with 5% DIEA in CH$_2$Cl$_2$ and washed according to the protocol described in Table 1. The solution of Boc-Arg(Tos)-OH (107 mg, 0.25 mmole) in DMF-CH$_2$Cl$_2$ (1:1) is shaken with the neutralized resin and DIC (44 μL, 0.275 mmole) in a manual solid phase peptide synthesis equipment for 1 hour. After the completion of the coupling reaction is proved by negative ninhydrin test, deprotection with 50% TFA in CH$_2$Cl$_2$, and neutralization with 5% DIEA in CH$_2$Cl$_2$, the peptide chain is built stepwise by adding the following protected amino acids in the indicated order on the resin to obtain the desired peptide sequence: Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Lys(2-Cl-Z)-OH, Boc-Arg(Tos)-OH, Boc-Ala-OH, Boc-Ser(Bzl)-OH, Boc-Leu-OH, Boc-Gln-OH, Boc-Ala-OH, Boc-Leu-OH, Boc-Val-OH, Boc-Lys(2-Cl-Z)-OH, Boc-Arg(Tos)-OH, Boc-Tyr(2,6-diCl-Z)-OH, Boc-Ser (Bzl)-OH, Boc-Asn-OH, Boc-Thr(Bzl)-OH, Boc-Phe(pCl)-OH, Boc-Ile-OH, Boc-Ala-OH, Boc-Asp(OcHx)-OH, Boc-D-Arg(Tos)-OH, Boc-Tyr(2,6-diCl-Z)-OH.

The protected amino acids (0.25 mmole each) are coupled with DIC (44 μL, 0.275 mmole) with the exceptions of Boc-Asn-OH and Boc-Gln-OH which are coupled with their preformed HOBt esters. After removal of the N$^\alpha$-Boc protecting group from Tyr$^1$, the peptide is acylated with phenylacetic acid (PhAc) (54 mg, 0.4 mmole) using DIC (70 μL, 0.44 mmole).

In order to cleave the peptide from the resin and deprotect it, the dried peptide resin (171 mg) is stirred with 0.5 mL m-cresol and 5 mL hydrogen fluoride (HF) at 0° C. for 1 hour. After evaporation of the HF under vacuum, the remnant is washed with dry diethyl ether and ethyl acetate. The cleaved and deprotected peptide is dissolved in 50% acetic acid and separated from the resin by filtration. After dilution with water and lyophilization, 98 mg crude product is obtained.

The crude peptide is checked by analytical HPLC using a Hewlett-Packard Model HP-1090 liquid chromatograph with a W-Porex C18 reversed-phase column (4.6×250 mm, 5 μm particle size, 300 Å pore size from Phenomenex, Rancho Palos Verdes, Calif.) and linear gradient elution, (e.g., 40–70% B) with a solvent system consisting of (A) 0.1% aqueous TFA and (B) 0.1% TFA in 70% aqueous MeCN. 60 mg of the crude peptide is dissolved in AcOH/H$_2$O, stirred, filtered and applied on a VYDAC 228TP column (10×250 mm) packed with C8 silica gel. The column is eluted with a solvent system described above in a linear gradient mode (e.g., 30–55% B in 120 min); flow rate 2 mL/min. The eluent is monitored at 220 nm, and fractions are examined by analytical HPLC. Fractions with purity higher than 95% are pooled and lyophilized to give 2.6 mg pure product. The analytical HPLC is carried out on a W-Porex C18 reversed-phase column described above using isocratic elution with a solvent system described above with a flow rate of 1.2 mL/min. The peaks are monitored at 220 and 280 nm. The peptide is judged to be substantially (>95%) pure by analytical HPLC. The expected amino acid composition is also confirmed by amino acid analysis.

Peptides 10, 11, 12, 13, and 14 are synthesized in the same manner as Peptide 9, except that these peptides also contain other substitutions, to yield:

[PhAc$^0$,Tyr(Me),D-Arg$^2$,Phe(pCl)$^6$Ala$^{15}$, Nle$^{27}$]hGH-RH (1–29)-NH$_2$ Peptide 10

[PhAc$^0$,D-Arg$^2$,Phe(pCl)$^6$,Abu$^8$,Ala$^{15}$,Nle$^{27}$],hGH-RH (1–29)NH$_2$ Peptide 11

[PhAc$^0$,D-Arg$^2$,Nal$^6$,Abu$^{8,28}$,Ala$^{15}$,Nle$^{27}$]hGH-RH(1–29) NH$_2$ Peptide 12

[PhAc$^0$,D-Arg$^2$,Phe(pCl)$^6$,Abu$^{8,28}$,Ala$^{15}$,Nle$^{27}$]hGH-RH (1–29)NH$_2$ Peptide 13

[PhAc$^0$,D-Arg$^2$,Phe(pCl)$^6$,Abu$^8$,D-Lys$^{12}$,Ala$^{15}$,Nle$^{27}$]hGH-RH(1–29)NH$_2$ Peptide 14

EXAMPLE VIII

PhAc-Tyr$^1$-D-Arg$^2$-Asp$^3$-Ala$^4$-Ile$^5$-Phe(pCl)$^6$-Thr$^7$-Ser$^8$-Ser$^9$-Tyr$^{10}$
-Arg$^{11}$-Lys$^{12}$-Val$^{13}$-Leu$^{14}$-Ala$^{15}$-Gln$^{16}$-Glu$^{17}$-Ser$^{18}$-Ala$^{19}$-Arg$^{20}$-Lys$^{21}$-
Leu$^{22}$-Leu$^{23}$-Gln$^{24}$-Asp$^{25}$-Ile$^{26}$-Nle$^{27}$-Ser$^{28}$-Arg$^{29}$-NH$_2$ Peptide 18 or cyclo$^{17,21}$[PhAc$^0$,D-Arg$^2$, Phe(pCl)$^6$,Ser$^8$,Ala$^{15}$,Glu$^{17}$,Nle$^{27}$]hGH-RH(1–29)NH$_2$ The synthesis is conducted in a stepwise manner using manual solid phase peptide synthesis equipment. Briefly, benzhydrylamine (BHA) resin (Bachem, Calif.) (100 mg, 0.044 mmole) is neutralized with 5% DIEA in CH$_2$Cl$_2$ and washed according to the protocol described in Table 1. The solution of Boc-Arg(Tos)-OH (107 mg, 0.25 mmole) in DMF-CH$_2$Cl$_2$ (1:1) is shaken with the neutralized resin and DIC (44 μL, 0.275 mmole) in a manual solid phase peptide synthesis equipment for 1 hour. After the completion of the coupling reaction is proved by negative ninhydrin test, deprotection with 50% TFA in CH$_2$Cl$_2$, and neutralization with 5% DIEA in CH$_2$Cl$_2$, the peptide chain is built stepwise by coupling the following protected amino acids in the indicated order on the resin to obtain the desired peptide sequence: Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Lys(Fmoc)-OH, Boc-Arg(Tos)-OH, Boc-Ala-OH, Boc-Ser(Bzl)-OH, Boc-Glu(Fm)-OH, Boc-Gln-OH, Boc-Ala-OH, Boc-Leu-OH, Boc-Val-OH, Boc-Lys(2-Cl-Z)-OH, Boc-Arg(Tos)-OH, Boc-Tyr(2,6-diCl-Z)-OH, Boc-Ser (Bzl)-OH, Boc-Ser(Bzl)-OH, Boc-Thr(Bzl)-OH, Boc-Phe (pCl)-OH, Boc-Ile-OH, Boc-Ala-OH, Boc-Asp(OcHx)-OH, Boc-D-Arg(Tos)-OH, Boc-Tyr(2,6-diCl-Z)-OH.

The protected amino acids (0.25 mmole each) are coupled with DIC (44 μL, 0.275 mmole) with the exceptions of Boc-Asn-OH and Boc-Gln-OH which are coupled with their preformed HOBt esters. After removal of the N$^\alpha$-Boc protecting group from Tyr$^1$, the peptide is acylated with phenylacetic acid (PhAc) (75 mg, 0.4 mmole) using DIC (70 μL, 0.44 mmole). The acylated peptide is deprotected with 20% piperidine in DMF for 1 plus 20 minutes to give free side-chains of Glu$^{17}$ and Lys$^{21}$. After washing the resin, lactam bridge is formed with HBTU reagent (110 mg, 0.275 mmole) in DMF-DCM (1:1) containing DIEA (137 μL, 0.55 mmole) and HOBt (39 mg, 0.275 mmole) for 3 hours (negative Kaiser ninhydrin test).

In order to cleave the peptide from the resin and deprotect it, the dried peptide resin (53.1 mg) is stirred with 0.5 mL m-cresol and 5 mL hydrogen fluoride (HF) at 0° C. for 1 hour. After evaporation of the HF under vacuum, the remnant is washed with dry diethyl ether and ethyl acetate. The cleaved and deprotected peptide is dissolved in 50% acetic acid and separated from the resin by filtration. After dilution with water and lyophilization, 13.7 mg crude product is obtained.

The crude peptide is checked by analytical HPLC using a Hewlett-Packard Model HP-1090 liquid chromatograph with a W-Porex C18 reversed-phase column (4.6×250 mm, 5 μm particle size, 300 Å pore size from Phenomenex, Rancho Palos Verdes, Calif.) and linear gradient elution, (e.g., 40–70% B) with a solvent system consisting of (A) 0.1% aqueous TFA and (B) 0.1% TFA in 70% aqueous MeCN. The crude peptide is dissolved in AcOH/H$_2$O, stirred, filtered and applied on a VYDAC 228TP column (10×250 mm) packed with C8 silica gel. The column is eluted with a solvent system described above in a linear gradient mode (e.g., 30–55% B in 120 min); flow rate 2 mL/min. The eluent is monitored at 220 nm, and fractions are examined by analytical HPLC. Fractions with purity higher than 95% are pooled and lyophilized to give 0.96 mg pure product. The analytical HPLC is carried out on a W-Porex C18 reversed-phase column described above using isocratic elution with a solvent system described above with a flow rate of 1.2 mL/min. The peaks are monitored at 220 and 280 nm. The peptide is judged to be substantially (>95%) pure by analytical HPLC. The expected amino acid composition is also confirmed by amino acid analysis.

Peptides 17, 19 and 20 are synthesized in the same manner as Peptide 18, except that in addition to other substitutions lactam bridge is formed between positions 8,12 or 25,29, to yield:

cyclo$^{8,12}$[PhAc$^0$, D-Arg$^2$, Phe(pCl)$^6$, Glu$^8$, Ala$^{15}$, Nle$^{27}$] hGH-RH(1–29)NH$_2$ Peptide # 17 cycl$^{25,28}$[PhAc$^0$, D-Arg$^2$, Phe(pCl)$^6$, Abu$^8$Ala$^{15}$, D-Asp$^{25}$, Nle$^{27}$, Orn$^{29}$]hGH-RH(1–29)NH$_2$ Peptide # 19 cyclo$^{25,29}$[PhAc$^0$, D-Arg$^2$,Nal$^6$, Abu$^8$, Ala$^{15}$, D-Asp$^{25}$, Nle$^{27}$, Orn$^{29}$]hGH-RH(1–29)NH$_2$ Peptide # 20

Peptides 21,22,23, and 24 are synthesized in the same manner as Peptide 18, except that in addition to other substitutions lactam bridge is formed between both 8,12 and 21,25 positions, to yield:

cyclo$^{8,12; 21,25}$[PhAc$^0$, D-Arg$^2$, Phe(pCl)$^6$, Glu$^{8,25}$, Abu$^{15}$, Nle$^{27}$]hGH-RH(1–28)Agm Peptide #21 cyclo$^{8,12;\ 21,25}$[PhAc$^0$, D-Arg$^2$, D-Asp$^3$, Phe(pCl)$^6$, Glu$^{8,25}$, D-Lys$^{12}$, Ala$^{15}$, Nle$^{27}$]hGH-RH(1–29)NH$_2$ Peptide # 22 cyclo$^{8,22;\ 21,25}$[PhAc$^0$, D-Arg$^2$, Phe(pCl)$^6$, Glu$^{8,25}$, D-Lys$^{12}$, Ala$^{15}$, Nle$^{27}$]hGH-RH(1–29)NH$_2$ Peptide # 23 cyclo$^{8,12;\ 21,25}$[PhAc$^0$, D-Arg$^2$, Phe(pCl)$^6$, Asp$^8$, D-Lys$^{12}$, Ala$^{15}$, Glu$^{25}$, Nle$^{27}$]hGH-RH(1–29)NH$_2$ Peptide # 24

EXAMPLE IX

Biological Activity

The peptides of the present invention were tested in an in vitro and in vivo assay for their ability to inhibit the hGH-RH(1–29)NH$_2$ induced GH release.

Superfused Rat Pituitary System. The analogues were tested in vitro in a test described earlier (S. Vigh and A. V. Schally, Peptides 5:241–347, 1984) with modification (Z. Rekasi and A. V. Schally, P. N. A. S. 90:2146–2149, 1993).

Briefly, the cells are preincubated with peptides for 9 minutes (3 mL) at various concentrations. Immediately after the incubation, 1 nM hGH-RH(1–29)NH$_2$ is administered for 3 minutes (1 mL) [0 minute response]. To check the duration of the antagonistic effect of the analogue, 1 nM hGH-RH(1–29)NH$_2$ is applied 30, 60, 90, and 120 minutes later for 3 minutes [30, 60, 90, 120 min responses]. Net integral values of the GH responses are evaluated. GH responses are compared to and expressed as percent of the original GH response induced by 1 nM GH-RH(1–29)NH$_2$. The effect of the new antagonists are compared to that of [Ac-Tyr$^1$,D-Arg$^2$]hGH-RH(1–29)NH$_2$, the "Standard antagonist".

Growth Hormone Radio-immunoassay. Rat GH levels in aliquots of undiluted and diluted superfusion samples were measured by double-antibody radioimmunoassay using materials supplied by the National Hormone and Pituitary Program, Baltimore, Md. The results of RIA were analyzed with a computer program developed in our institute (V. Csernus and A. V. Schally, Harwood Academic (Greenstein, B. C. ed., London, pp. 71–109, 1991), hereby incorporated by reference. Inter-assay variation was less than 15% and intra-assay variation was less than 10%.

GH-RH Binding Assay. A sensitive radioreceptor binding assay was developed to determine the binding characteristics of the antagonists of GH-RH (G. Halmos, A. V. Schally et al., Receptor 3, 87–97, 1993), hereby incorporated by reference. The assay is based on binding of labelled [His$^1$, Nle$^{27}$]hGH-RH(1–32)NH$_2$ to rat anterior pituitary membrane homogenates. Iodinated derivatives of [His$^1$, Nle$^{27}$] hGH-RH(1–32)NH$_2$ are prepared by the chloramine-T method (F. C. Greenwood et al., Biochemistry 89:114–123, 1963), hereby incorporated by reference. Pituitaries from male Sprague-Dawley rats (250–300 g) are used to prepare crude membranes. For saturation binding analyses, membrane homogenates are incubated with at least 6 concentrations of [His$^{1,125}$I-Tyr$^{10}$,Nle$^{27}$]hGH-RH(1–32)NH$_2$, ranging from 0.005 to 0.35 nM in the presence or absence of excess unlabelled peptide (1 µM).

The pellet is counted for radioactivity in a γ-counter. The affinities of the antagonist peptides tested to rat pituitary GH-RH receptors are determined in competitive binding experiments. The final binding affinities are estimated by K$_i$(dissociation constant of the inhibitor-receptor complex) and are determined by the Ligand PC computer program of Munson and Rodbard as modified by McPherson. Relative affinities compared to [Ac-Tyr$^1$, D-Arg$^2$]hGH-RH(1–29)NH$_2$, the Standard antagonist, are calculated as the ratio of K$_i$ of the tested GH-RH antagonist to the K$_i$ of the Standard antagonist.

In Vivo Tests. Adult male Sprague-Dawley rats are anesthetized with pentobarbital (6 mg/100 g b.w., i.p.). Blood samples are taken from the jugular vein 30 min after the injection of pentobarbital. One group of 7 animals receives hGH-RH(1–29)NH$_2$ as control. Other groups of rats are injected with [Ac-Tyr$^1$,D-Arg$^2$]hGH-RH(1–29)NH$_2$ as Standard antagonist, or with one of the antagonist peptide 30 seconds prior to hGH-RH(1–29)NH$_2$, which is administered at dose of 2–3 µg/kg b.w. Blood samples are taken from the jugular vein 5 and 15 min after the injection of antagonists. GH levels are measured by RIA. Potencies of the antagonists are calculated by the factorial analysis of Bliss and Marks with 95% confidence limits and are based on the doses of 100 and 400 µg/kg b.w. of the Standard antagonist and 20 and 80 µg/kg b.w. of the antagonists tested. Statistical significance was assessed by Duncan's new multiple range test.

Results in vitro. The results of the in vitro antagonistic activities tested in superfused rat pituitary system and binding assay are summarized in Table II and Table III, respectively. As can be seen from these data, acylation of the analogs with PhAc or Ibu which contain D-Arg$^2$ substitution combined with Phe(pCl)$^6$ or Nal$^6$, Abu$^8$, Abu15 or Ala$^{15}$, Nle$^{27}$, Asp$^{28}$, Agm$^{29}$ or Arg$^{29}$-NH$_2$, and/or lactam bridge cause an immense increase in receptor binding as well as in inhibition of GH release in vitro and in vivo. Antagonists [PhAc$^0$, D-Arg$^2$, pCl-Phe$^6$, Abu$^{15}$, Nle$^{27}$]hGH-RH(1–28) Agm(MZ-5–156), [PhAc$^0$-, D-Arg$^2$, Phe(pCl)$^6$, Abu$^{8,28}$, Ala$^{15}$, Nle$^{27}$]hGH-RH(1–29)NH$_2$(MZ-5–208), [PhAc$^0$-, D-Arg$^2$, Phe(pCl)$^6$, Abu$^8$, Ala$^{15}$, Nle$^{27}$]hGH-RH(1–29)NH$_2$ (MZ-5–192), [PhAc$^0$, D-Arg$^2$, Phe(pCl)$^6$, Ala$^{15}$, Nle$^{27}$, Asp$^{28}$]hGH-RH(1–28)Agm(MZ-5–116), and cyclo 17,21 [PhAc$^0$, D-Arg$^2$, Phe(pCl)$^6$, Ser$^8$, Ala$^{15}$,Glu$^{17}$,Nle$^2$]hGH-RH(1–29)NH$_2$ are the most effective antagonists in vitro.

Results in vivo. Table IV shows the serum GH levels in rats pretreated with GH-RH antagonists. Peptides 7, 8, 9, 11, 13, and 18 produce a significant greater and longer-lasting inhibition of the GH release stimulated by hGH-RH(1–29) NH$_2$ than the standard antagonist. In vivo experiments, Peptide 8 (MZ-5–156) inhibits hGH-RH(1–29)NH$_2$-induced GH-release to greater extent than MZ-4–71,[Ibu$^0$,D-Arg$^2$, Phe(pCl)$^6$,Abu$^{15}$,Nle$^{27}$]hGH-RH(1–28)Agm, the previously most effective antagonist.

TABLE II

Inhibition of GH Release in Superfused Rat Pituitary System

| Peptide | Dose (nM) | Inhibition of GH release (%) | | | | |
|---|---|---|---|---|---|---|
| | | 0 min | 30 min | 60 min | 90 min | 120 min |
| Standard antagonist | 100 | 62.1 | 2.5 | 19 | | |
| Peptide 1 | 3 | 60.1 | 12.4 | 11.5 | | |
| | 30 | 98 | 49.2 | 37.6 | | |
| Peptide 2 | 3 | 27.4 | 16.2 | 48.4 | 30.2 | |
| | 30 | 94.7 | 53.0 | 24.4 | 41.8 | |
| Peptide 3 | 30 | 97.4 | 32.2 | 35.9 | 42.1 | |
| Peptide 4 | 3 | 28 | 21.3 | 15 | | |
| | 30 | 76.7 | 53.4 | 32 | | |
| Peptide 5 | 30 | 97.1 | 93.9 | 80.1 | 56.9 | |
| Peptide 6 | 30 | 86.3 | 89.9 | 78.9 | 87.6 | 62.7 |
| Peptide 7 | 30 | 96.3 | 41.5 | 21.5 | 23.2 | 20.6 |
| Peptide 8 | 3 | 78.8 | 73.3 | 65.9 | 54.9 | |
| | 10 | 88.8 | 83.5 | 64.9 | 51.7 | 42.3 |
| | 30 | 94.5 | 90.0 | 71.5 | 65.0 | 55.6 |
| Peptide 9 | 30 | 92.0 | 80.6 | 58.9 | 46.7 | 46.0 |
| Peptide 10 | 30 | 84.8 | 35.2 | 38.2 | 29.8 | 33.8 |
| Peptide 11 | 30 | 92.3 | 80.9 | 73.3 | 63.2 | 55.7 |
| Peptide 15 | 30 | 85.5 | 65.2 | 56.1 | 44.0 | 46.7 |
| Peptide 16 | 30 | 85.2 | 12.3 | 25.1 | 14.8 | 36.0 |
| Peptide 12 | 30 | 87.0 | 61.0 | 37.0 | 34.0 | 41.0 |
| Peptide 13 | 30 | 92.3 | 90.0 | 77.3 | 64.7 | 61.1 |

TABLE II-continued

Inhibition of GH Release in Superfused Rat Pituitary System

| Peptide | Dose (nM) | Inhibition of GH release (%) | | | | |
|---|---|---|---|---|---|---|
| | | 0 min | 30 min | 60 min | 90 min | 120 min |
| Peptide 14 | 30 | 87.0 | 32.0 | 6.0 | 12.0 | 24.0 |
| Peptide 17 | 30 | 87.3 | 46.4 | 10.7 | 17.4 | |
| Peptide 18 | 30 | 96.8 | 79.4 | 68.3 | 47.1 | |
| Peptide 21 | 30 | 79.6 | 56.5 | 47.5 | 53.4 | |
| Peptide 22 | 30 | 65.8 | 37.7 | 24.9 | 26.8 | |
| Peptide 23 | 30 | 54.5 | 28.3 | 16.3 | 21.0 | |
| Peptide 19 | 30 | 17.5 | 0.0 | 11.2 | 14.0 | |
| Peptide 20 | 30 | 11.0 | 0.0 | 0.0 | 13.0 | |
| Peptide 24 | 30 | 46.0 | 6.0 | 26.0 | 31.0 | |

TABLE III $K_i$ values and relative affinities (R.A) of hGH-RH antagonists

| Peptide | K (nM) | R.A. |
|---|---|---|
| Standard | 3.37 ± 0.14 | 1 |
| Peptide 3 | 0.301 ± 0.14 | |
| Peptide 5 | 0.096 | 11.19 |
| Peptide 8 | 0.0159 ± 0.01 | 35.10 |
| Peptide 18 | 0.159 ± 0.04 | 21.19 |
| Peptide 11 | 0.059 ± 0.001 | 57.12 |
| Peptide 23 | 0.456 | 7.39 |

TABLE IV

Serum Growth Hormone Levels in Rats Pretreated with Different GH-RH Antagonsists at Different Time Intervals Prior to GH-RH (1–29) $NH_2$ at a Dose of 3 μg/kg

| Treatment Inhibition (intravenously) | | Dose (μg/kg) | Serum GH Levels | |
|---|---|---|---|---|
| | | | (ng/mL) | % |
| GH-RH (1–29) $NH_2$ | | 3.0 | 695.15 ± 95.40 | 0% |
| Peptide 18 | 2 min | 80 | 370.31 ± 48.26 | 47%** |
| | 15 min | 80 | 564.74 ± 76.99 | N.S. |
| Peptide 9 | 2 | 80 | 450.21 ± 68.38 | 35% |
| GH-RH (1–29) $NH_2$ | | 3.0 | 703.34 ± 90.01 | 0% |
| Peptide 8 | 2 min | 80 | 177.13 ± 31.75** | 75% |
| | 15 min | 80 | 183.91 ± 26.19** | 74% |
| GH-RH (1–29) $NH_2$ | | 3.0 | 724.68 ± 93.01 | 0% |
| Peptide 8 | 30 min | 80 | 567.46 ± 50.70 | 22% NS |
| | 60 min | 80 | 582.41 ± 70.18 | 20% NS |
| GH-RH (1–29) $NH_2$ | | 3.0 | 883.36 ± 148.34 | 0% |
| Peptide 13 | 2 min | 80 | 316.01 ± 68.24** | 64% |
| | 15 min | 80 | 641.73 ± 92.01* | 27% |
| GH-RH (1–29) $NH_2$ | | 3.0 | 703.34 ± 93.01 | 0% |
| Peptide 7 | 2 min | 80 | 611.07 ± 87.75* | 31% |
| | 15 min | 80 | 688.39 ± 107.91 | N.S. |
| GH-RH (1–29) $NH_2$ | | 3.0 | 724.68 ± 93.01 | 0% |
| Peptide A | 15 min | 80 | 585.33 ± 89.34* | 43% |
| | 30 min | 80 | 788.39 ± 96.93 | 23% NS |

TABLE IV-continued

Serum Growth Hormone Levels in Rats Pretreated with Different GH-RH Antagonsists at Different Time Intervals Prior to GH-RH (1–29) $NH_2$ at a Dose of 3 μg/kg

| Treatment Inhibition (intravenously) | Dose (μg/kg) | Serum GH Levels | |
|---|---|---|---|
| | | (ng/mL) | % |

Data are expressed as mean ± SEM
*p < 0.05 vs control
**p < 0.01 vs control
NS not significant Effect of GH RH antagonists on SW 1990 human pancreatic cancers in nude mice Small pieces of an SW-1990 rumor growing in a nude mouse were transplated s.c. into the right flanks of 60 nu/nu male nude mice. Ten days after transplantation, 40 mice with well growing tumors were groupled into 4 groups with equal average tumor volume (16 mm$^3$) in each group. Treatment started 13 days after transplantation and was continuted for 44 days. Groups are shown in the table. The tumors were measured and volume was calculated weekly. Tumor volume changes are shown in Table V. On day 45 of treatment the mice were sacraficed under Metofane anesthesia by exsanguination from abdominal aorta. Blood was collected, tumor and organ weights were determined.

Histology, receptor studies and determination of blood hormone levels are in progress.

Results

Tumor volume data and tumor weights at the end of the experiment are shown in the table. Treatment with 10 μg/day of Peptide #8 resulted in a significant inhibition of growth of SW-1990 cancers as shown by volume and weigth data. Peptide A had no significant effect on the tumors. Body, liver, kidney and spleen weights showed no significant differences from control values.

Effect of treatment with GH-RH antagonists on tumor weights and final tumor volume of SW-1990 humane pancreatic cancers growing in nude mice.

TABLE V

| Group No. | Treatment | Dose mg/day | Number of mice | Tumor weights (mg) | Final Tumor Volume mm$^3$ |
|---|---|---|---|---|---|
| 1 | Control | | 10 | 1467 ± 374 | 1291 ± 301 |
| 2 | Peptide A | 10 | 10 | 1467 ± 595 | 1183 ± 342 |
| 3 | Peptide A | 40 | 10 | 1297 ± 258 | 902 ± 156 |
| 4 | Peptide B | 10 | 10 | 931 ± 330 | 612 ± 220* |

*p < 0.05
Peptide A: [Ibu$^0$—D—Arg$^2$—Phe(pCl)$^6$—Abu$^{16}$—Nle$^{27}$] hGHRH (1–28) Agm

We claim:

1. A compound having the formula [Ibu$^0$,D-Arg$^2$,Phe(pCl)$^{8,10}$,Abu$^{15}$,Nle$^{27}$]hGH-RH(1–28)Agm.

2. A compound of having the formula [PhAc$^0$,D-Arg$^2$,Phe(pCl)$^8$,Abu$^{15}$,Nle$^{27}$]hGH-RH(1–28)Agm.

3. A compound having the formula [PhAc$^0$,D-Arg$^2$, Phe(pCl)$^6$,Abu$^8$,Ala$^{15}$,Nle$^{27}$]hGH-RH(1–29)NH$_2$.

4. A compound having the formula [PhAc$^0$,D-Arg$^2$,Phe(pCl)$^6$,Abu$^{8,28}$,Ala$^{15}$,Nle$^{27}$]hGH-RH(1–29)-NH$_2$.

5. A compound of claim 1 selected from the group consisting of cyclo$^{8,12}$[PhAc$^0$,D-Arg$^2$,Phe(pCl)$^6$,Glu$^8$,Ala$^{15}$,Nle$^{27}$] hGH-RH(1–29)-NH$_2$, cyclo$^{17,21}$[PhAc$^0$,D-Arg$^2$,Phe(pCl)$^6$,Ser$^8$,Ala$^{15}$,Glu$^{17}$, Nle$^{27}$]hGH-RH(1–29)-NH$_2$, cyclo$^{8,12;\ 21,25}$[PhAc$^0$,D-Arg$^2$,Phe(pCl)$^6$,Glu$^{8,25}$,Abu$^{15}$, Nle$^{27}$]hGH-RH(1–28)Agm, cyclo$^{8,12;\ 21,25}$[[PhAc$^0$,D-Arg$^2$,D-Asp$^3$,Phe(pCl)$^6$,Glu$^{8,}$$_{25}$,D-lys$^{12}$,Ala$^{15}$,Nle$^{27}$]hGH-RH(1–29)-NH$_2$, and cyclo$^{8,12;\ 21,25}$[[PhAc$^0$,D-Arg$^2$,Phe(pCl)$^6$,Glu$^{8,25}$ ,D-Lys$^{12}$,Ala$^{15}$,Nle$^{27}$]hGH-RH(1–29)-NH$_2$.

6. A compound of claim 5 having the formula cyclo$^{8,12}$ [PhAc$^0$,D-Arg$^2$,Phe(pCl)$^6$,Glu$^8$,Ala$^{15}$,Nle$^{27}$]hGH-RH(1–29)-NH$_2$.

7. A compound of claim 5 having the formula cyclo$^{17,21}$ [PhAc$^0$,D-Arg$^2$,Phe(pCl)$^6$,Ser$^8$,Ala$^{15}$,Glu$^{17}$,Nle$^{27}$]hGH-RH(1–29)-NH$_2$.

8. A compound of claim 5 having the formula cyclo$^{8,12;\ 21,25}$[PhAc$^0$,D-Arg$^2$,Phe(pCl)$^6$,Glu$^{8,25}$,Abu$^{15}$,Nle$^{27}$]hGH-RH(1–28)Agm.

9. A compound of claim 5 having the formula cyclo$^{8,12;\ 21,25}$[[PhAc$^0$,D-Arg$^2$,D-Asp$^3$,Phe(pCl)$^6$,Glu$^{8,25}$,D-Lys$^{12}$, Ala$^{15}$,Nle$^{27}$]hGH-RH(1–29)-NH$_2$.

10. A compound of claim 5 having the formula cyclo$^{8,12;\ 21,25}$[[PhAc$^0$,D-Arg$^2$,Phe(pCl)$^6$,Glu$^{8,25}$,D-Lys$^{12}$,Ala$^{15}$, Nle$^{27}$]hGH-RH(1–29)-NH$_2$.

11. A method of suppressing excessive levels of GH in a patient in need of same which comprises administering said patient an effective amount of a compound in accordance with claim 5.

12. A method of claim 11 wherein the patient is a patient having a cancer carrying receptors for IGF-I.

13. A method of suppressing excessive levels of GH in a patient in need of same which comprises administering said patient an effective amount of a compound of claim 1.

14. A method of claim 13 wherein the patient is a patient having a cancer carrying receptors for IGF-I.

15. A method of suppressing excessive levels of GH in a patient in need of same which comprises administering said patient an effective amount of a compound of claim 2.

16. A method of claim 15 wherein the patient is a patient having a cancer carrying receptors for IGF-I.

17. A method of suppressing excessive levels of GH in a patient in need of same which comprises administering said patient an effective amount of a compound of claim 3.

18. A method of claim 17 wherein the patient is a patient having a cancer carrying receptors for IGF-I.

19. A method of suppressing excessive levels of GH in a patient in need of same which comprises administering said patient an effective amount of a compound of claim 4.

20. A method of claim 19 wherein the patient is a patient having a cancer carrying receptors for IGF-I.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 29
        (B) TYPE:Amino
        (C) STRANDEDNESS:Unknown
        (D) TOPOLOGY:Unknown (ii) MOLECULE TYPE: peptide (ix) FEATURE:
        (D) OTHER INFORMATION: A lactam bridge is
            formed between any one of the pairs of positions
            1,2; 2,3;8,12; 16,20; 17-21; 21,25; 25,29 or both
            8,12 and 21,25 positions.
            X  attached to position 1 is  H, Ac, Aqc, IAc,
            BrProp, For, Ibu, Nac, 2-Nac, 1- or 2-Npt, 1- or
            2-Npr, PhAc, Fpr, or any other aromatic or
            nonpolar acyl group,
            Xaa1 is Glu,
            Gln, Asp, Asn, Abu, Leu, Tyr, His,Phe(Y), in
            which Y=H, F, Cl, Br, NO2, NH2, CH3 or OCH3 as a
            substituent in the phenyl ring thereof, Ser, Thr,
            Val, Ile, Ala, Abu, Nle, or Aib,
            Xaa2 is Lys, Arg, Orn, or Agmatine,
            Xaa3 is Glu,
            Gln, Asp, Asn, Abu, Leu, Tyr, His, Phe(Y), in
            which Y=H, F, Cl, Br, NO2, NH2, CH3 or OCH3 as a
            substituent in the phenyl ring thereof, Ser, Thr,
            Val, Ile, Ala, Abu, Nle, or Aib,
            Xaa4 is Ala, Abu or Gly,
            Xaa5 is Ile, Ala or Gly,
            Xaa6 is Phe, 1,2,3,4,-tetrahydrisoquinoline,
            2,3,4,9-tetrahydro-1H-pyrido[3,4-b]indol-3-
            carboxylic acid, 2-naphthylalanine or Phe(Y), in
            which Y=H, F, Cl, Br, NO2, NH2, CH3 or OCH3, as a
            substituent in the phenyl ring thereof,
            Xaa8 is Glu,
            Gln, Asp, Asn, Abu, Leu, Tyr, His, Phe(Y), in
            which Y=H, F, Cl, Br, NO2, NH2, CH3 or OCH3 as a
            substituent in the phenyl ring thereof, Ser, Thr,
            Val, Ile, Ala, Abu, Nle, or Aib,
            Xaa10 is Tyr or Phe(Y), in which Y=H, F, Cl, Br,
            NO2, NH2, CH3 or OCH3, as a substituent in the
            phenyl ring thereof,
            Xaa11 is Arg or 2-amino-5-ureidovaleric acid
            Xaa12 is Lys, Arg, Orn, or Agmatine,
            Xaa15 is Gly, Ala, Abu or Gln,
            Xaa16 is Glu,
            Gln, Asp, Asn, Abu, Leu, Tyr, His, Phe(Y), in
            which Y=H, F, Cl, Br, NO2, NH2, CH3 or OCH3 as a
            substituent in the phenyl ring thereof, Ser, Thr,
            Val, Ile, Ala, Abu, Nle, or Aib,
            Xaa17 is Glu,
            Gln, Asp, Asn, Abu, Leu, Tyr, His, Phe(Y), in
            which Y=H, F, Cl, Br, NO2, NH2, CH3 or OCH3 as a
            substituent in the phenyl ring thereof, Ser, Thr,
            Val, Ile, Ala, Abu, Nle, or Aib,
            Xaa19 is Ala or Abu,
            Xaa20 is Lys, Arg, Orn, or Agmatine,
            Xaa21 is Lys, Arg, Orn, or Agmatine,
            Xaa25  is Glu,
            Gln, Asp, Asn, Abu, Leu, Tyr, His, Phe(Y), in
            which Y=H, F, Cl, Br, NO2, NH2, CH3 or OCH3 as a
            substituent in the phenyl ring thereof, Ser, Thr,
            Val, Ile, Ala, Abu, Nle, or Aib,
            Xaa27 is Met, Nle or Abu,
            Xaa28 is Ser, Asn, Asp, Ala or Abu,
            Xaa29 is Lys, Arg, Orn, or Agmatine.

(xi) SEQUENCE DESCRIPTION: SEQ ID NO: 1:

```
Xaa Xaa Xaa Xaa Xaa Xaa Thr Xaa Ser Xaa Xaa
 1               5                   10

Xaa Val Leu Xaa Xaa Ser Xaa Xaa Xaa Leu
            15              20

Leu Gln Xaa Ile Xaa Xaa Xaa
        25
```